United States Patent
Cartlidge et al.

(10) Patent No.: US 7,439,478 B2
(45) Date of Patent: *Oct. 21, 2008

(54) IMAGING SYSTEM, METHODOLOGY, AND APPLICATIONS EMPLOYING RECIPROCAL SPACE OPTICAL DESIGN HAVING AT LEAST ONE PIXEL BEING SCALED TO ABOUT A SIZE OF A DIFFRACTION-LIMITED SPOT DEFINED BY A MICROSCOPIC OPTICAL SYSTEM

(75) Inventors: Andrew G. Cartlidge, Palm Beach Gardens, FL (US); Howard Fein, Richmond Heights, OH (US)

(73) Assignees: Palantyr Research, LLC, Cleveland, OH (US); Angkor Technology, LLP, Cleveland, OH (US); Himanshu S. Amin, Solon, OH (US); Daniel B. Bortnick, Mentor, OH (US); Gregory Turocy, Moreland Hills, OH (US)

( * ) Notice: Subject to any disclaimer, the term of this patent is extended or adjusted under 35 U.S.C. 154(b) by 15 days.

This patent is subject to a terminal disclaimer.

(21) Appl. No.: 10/758,739

(22) Filed: Jan. 16, 2004

(65) Prior Publication Data
US 2004/0159772 A1 Aug. 19, 2004

Related U.S. Application Data

(63) Continuation-in-part of application No. 10/189,326, filed on Jul. 2, 2002, now Pat. No. 7,132,636, which is a continuation-in-part of application No. 09/900,218, filed on Jul. 6, 2001, now Pat. No. 6,664,528.

(51) Int. Cl.
*H01L 27/00* (2006.01)
(52) U.S. Cl. .................................. 250/208.1; 250/216

(58) Field of Classification Search .............. 250/208.1, 250/216, 306, 307; 396/111–114; 348/335, 348/340; 359/362, 363, 368, 385
See application file for complete search history.

(56) References Cited

U.S. PATENT DOCUMENTS 4,750,022 A  6/1988  Araki (Continued)

FOREIGN PATENT DOCUMENTS

GB  2216744 A  * 10/1989

OTHER PUBLICATIONS

International Search Report dated Nov. 12, 2002 in PCT Application No. PCT/US02/21392 filed Jul. 3, 2002.

(Continued)

*Primary Examiner*—Que T Le
(74) *Attorney, Agent, or Firm*—Amin, Turocy & Calvin, LLP

(57) ABSTRACT

An imaging system, methodology, and various applications are provided to facilitate optical imaging performance. The system includes a sensor having one or more receptors and an image transfer medium to scale the sensor and receptors in accordance with resolvable characteristics of the medium. A computer, memory, and/or display associated with the sensor provides storage and/or display of information relating to output from the receptors to produce and/or process an image, wherein a plurality of illumination sources can also be utilized in conjunction with the image transfer medium. The image transfer medium can be configured as a k-space filter that correlates a pitch associated with the receptors to a diffraction-limited spot associated with the image transfer medium, wherein the pitch can be unit-mapped to about the size of the diffraction-limited spot.

20 Claims, 16 Drawing Sheets

U.S. PATENT DOCUMENTS

| | | | |
|---|---|---|---|
| 5,051,770 A | 9/1991 | Cornuejols | |
| H1060 H | 5/1992 | Lazich | |
| 5,198,653 A | 3/1993 | Shen et al. | |
| 5,204,770 A | 4/1993 | Kachru et al. | |
| 5,291,008 A | 3/1994 | Havens et al. | |
| 5,430,807 A | 7/1995 | Gravely | |
| 5,559,629 A | 9/1996 | Sheets et al. | |
| 5,710,430 A | 1/1998 | Nuss | |
| 5,719,620 A | 2/1998 | Allio | |
| 5,737,084 A | 4/1998 | Ishihara | |
| 5,757,425 A | 5/1998 | Barton et al. | |
| 5,769,076 A * | 6/1998 | Maekawa et al. | 600/322 |
| 5,798,519 A * | 8/1998 | Vock et al. | 250/206.1 |
| 5,876,327 A | 3/1999 | Tsuyuki et al. | |
| 5,973,844 A | 10/1999 | Burger | |
| 6,005,916 A | 12/1999 | Johnson et al. | |
| 6,008,945 A | 12/1999 | Fergason | |
| 6,020,988 A | 2/2000 | Deliwala et al. | |
| 6,078,390 A | 6/2000 | Bengtsson | |
| 6,088,097 A | 7/2000 | Uhl | |
| 6,124,974 A | 9/2000 | Burger | |
| 6,128,068 A | 10/2000 | Suzuki et al. | |
| 6,178,346 B1 | 1/2001 | Amundson et al. | |
| 6,195,213 B1 | 2/2001 | Omura et al. | |
| 6,248,988 B1 | 6/2001 | Krantz | |
| 6,249,360 B1 | 6/2001 | Pollard et al. | |
| 6,268,918 B1 | 7/2001 | Tanabe et al. | |
| 6,285,811 B1 | 9/2001 | Aggarwal et al. | |
| 6,344,893 B1 | 2/2002 | Mendlovic et al. | |
| 6,448,556 B1 | 9/2002 | Cowley et al. | |
| 6,711,283 B1 * | 3/2004 | Soenksen | 382/133 |
| 2002/0110077 A1 * | 8/2002 | Drobot et al. | 369/112.27 |
| 2002/0110320 A1 | 8/2002 | Carlisle et al. | |
| 2002/0126591 A1 | 9/2002 | Kouichi et al. | |
| 2002/0162973 A1 | 11/2002 | Cordingley et al. | |
| 2003/0026762 A1 * | 2/2003 | Malmros et al. | 424/9.6 |

OTHER PUBLICATIONS

Melles Griot, Optical Systems, Machine Vision Product Guide, USA, 1998.

* cited by examiner

IMAGING SYSTEM, METHODOLOGY, AND APPLICATIONS EMPLOYING RECIPROCAL SPACE OPTICAL DESIGN HAVING AT LEAST ONE PIXEL BEING SCALED TO ABOUT A SIZE OF A DIFFRACTION-LIMITED SPOT DEFINED BY A MICROSCOPIC OPTICAL SYSTEM

RELATED APPLICATION

This application is a continuation-in-part of U.S. patent application Ser. No. 10/189,326 which was filed Jul. 2, 2002 now U.S. Pat. No. 7,132,636 entitled IMAGING SYSTEM AND METHODOLOGY EMPLOYING RECIPROCAL SPACE OPTICAL DESIGN, which is a continuation-in-part of U.S. patent application Ser. No. 09/900,218, which was filed Jul. 6, 2001 now U.S. Pat. No. 6,664,528, entitled IMAGING SYSTEM AND METHODOLOGY EMPLOYING RECIPROCAL SPACE OPTICAL DESIGN, both of which are incorporated herein by reference.

TECHNICAL FIELD

The present invention relates generally to image and optical systems, and more particularly to a system and method to facilitate imaging performance via an image transfer medium that projects characteristics of a sensor to an object field of view.

BACKGROUND OF THE INVENTION

Microscopes facilitate creating a large image of a tiny object. Greater magnification can be achieved if the light from an object is made to pass through two lenses compared to a simple microscope with one lens. A compound microscope has two or more converging lenses, placed in line with one another, so that both lenses refract the light in turn. The result is to produce an image that is magnified with improved quality in Resolved Magnification and other image parameters than either lens could alone. Light illuminating the object first passes through a short focal length lens or lens group, called the objective, and then travels on some distance before being passed through a longer focal length lens or lens group, called the eyepiece. A lens group is often simply referred to singularly as a lens. Usually these two lenses are held in paraxial relationship to one another, so that the axis of one lens is arranged to be in the same orientation as the axis of the second lens. It is the nature of the lenses, their properties, their relationship, and the relationship of the objective lens to the object that determines how a highly magnified image is produced in the eye of the observer.

The first lens or objective is usually a small lens with a very small focal length. A specimen or object is placed in the path of a light source with sufficient intensity to illuminate as desired. The objective lens is then lowered until the specimen is very close to, but not quite at the focal point of the lens. Light leaving the specimen and passing through the objective lens produces a real, inverted and magnified image behind the lens, in the microscope at a point generally referred to as the intermediate image plane. The second lens or eyepiece has a longer focal length and is placed in the microscope so that the image produced by the objective lens falls closer to the eyepiece than one focal length (that is, inside the focal point of the lens). The image from the objective lens now becomes the object for the eyepiece lens. As this object is inside one focal length, the second lens refracts the light in such a way as to produce a second image that is virtual, inverted and magnified. This is the final image seen by the eye of the observer.

Alternatively, common infinity space or infinity corrected design microscopes employ objective lenses with infinite conjugate properties such that the light leaving the objective is not focused, but is a flux of parallel rays which do not converge until after passing through a tube lens where the projected image is then located at the focal point of the eyepiece for magnification and observation. Many microscopes, such as the compound microscope described above, are designed to provide images of certain quality to the human eye through an eyepiece. Connecting a Machine Vision Sensor, such as a Charge Coupled Device (CCD) sensor, to the microscope so that an image may be viewed on a monitor presents difficulties. This is because the image quality provided by the sensor and viewed by a human eye decreases as compared to an image viewed by a human eye directly through an eyepiece. As a result, conventional optical systems for magnifying, observing, examining, and analyzing small items often require the careful attention of a technician monitoring the process through an eyepiece. It is for this reason, as well as others, that Machine-Vision or computer-based image displays from the aforementioned image sensor displayed on a monitor or other output display device are not of quality perceived by the human observer through the eyepiece.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The present invention relates to a system and methodology that facilitates imaging performance of optical imaging systems. In regard to several optical and/or imaging system parameters, many orders of performance enhancement can be realized over conventional systems (e.g., greater effective resolved magnification, larger working distances, increased absolute spatial resolution, increased spatial field of view, increased depth of field, Modulation Transfer Function of about 1, oil immersion objectives and eye pieces not required). This is achieved by adapting an image transfer medium (e.g., one or more lenses, fiber optical media, or other media) to a sensor having one or more receptors (e.g., pixels) such that the receptors of the sensor are effectively scaled (e.g., "mapped", "sized", "projected", "matched", "reduced") to occupy an object field of view at about the scale or size associated with a diffraction limited point or spot within the object field of view. Thus, a band-pass filtering of spatial frequencies in what is known as Fourier space or "k-space" is achieved such that the projected size (projection in a direction from the sensor toward object space) of the receptor is filled in k-space.

In other words, the image transfer medium is adapted, configured and/or selected such that a transform into k-space is achieved, wherein an a priori design determination causes k-space or band-pass frequencies of interest to be substantially preserved throughout and frequencies above and below the k-space frequencies to be mitigated. It is noted that the frequencies above and below the k-space frequencies tend to cause blurring and contrast reduction and are generally associated with conventional optical system designs which define intrinsic constraints on a Modulation Transfer Function and "optical noise". This further illustrates that the systems and methods of the present invention are in contravention or opposition to conventional geometric paraxial ray designs. Consequently, many known optical design limitations associated with conventional systems are mitigated by the present invention.

According to one aspect of the present invention, a "k-space" design, system and methodology is provided which defines a "unit-mapping" of the Modulation Transfer Function (MTF) of an object plane to image plane relationship. The k-space design projects image plane pixels or receptors forward to the object plane to promote an optimum theoretical relationship. This is defined by a substantially one-to-one correspondence between image sensor receptors and projected object plane units (e.g., units defined by smallest resolvable points or spots in an optical or image transfer medium) that are matched according to the receptor size. The k-Space design defines that "unit-mapping" or "unit-matching" acts as an effective "Intrinsic Spatial Filter" which implies that spectral components of both an object and an image in k-space (also referred to as "reciprocal-space") are substantially matched or quantized. Advantages provided by the k-space design result in a system and methodology capable of much higher effective resolved magnification with concomitantly related and much increased Field Of View, Depth Of Field, Absolute Spatial Resolution, and Working Distances utilizing dry objective lens imaging, for example, and without employing conventional oil immersion techniques having inherent intrinsic limitations to the aforementioned parameters.

One aspect of the present invention relates to an optical system that includes an optical sensor having an array of light receptors having a pixel pitch. A lens optically associated with the optical sensor is configured with optical parameters functionally related to the pitch and a desired resolution of the optical system. As a result, the lens is operative to substantially map a portion of an object having the desired resolution along the optical path to an associated one of the light receptors.

Another aspect of the present invention relates to a method of designing an optical system. The method includes selecting a sensor with a plurality of light receptors having a pixel pitch. A desired minimum spot size resolution is selected for the system and a lens configured or an extant lens selected with optical parameters based on the pixel pitch and the desired minimum spot size is provided so as to map the plurality of light receptors to part of the image according to the desired resolution.

The present invention can be employed in various portable, stand-alone, or a combination of portable and stand-alone applications. For example, this can include portable imaging systems that can be distributed throughout the world to support various remote imaging applications. Such applications can include remote medicine or industrial applications whereby an image is generated in one location and transmitted to another location for analysis (e.g., remote pathology application).

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

Figure 1:
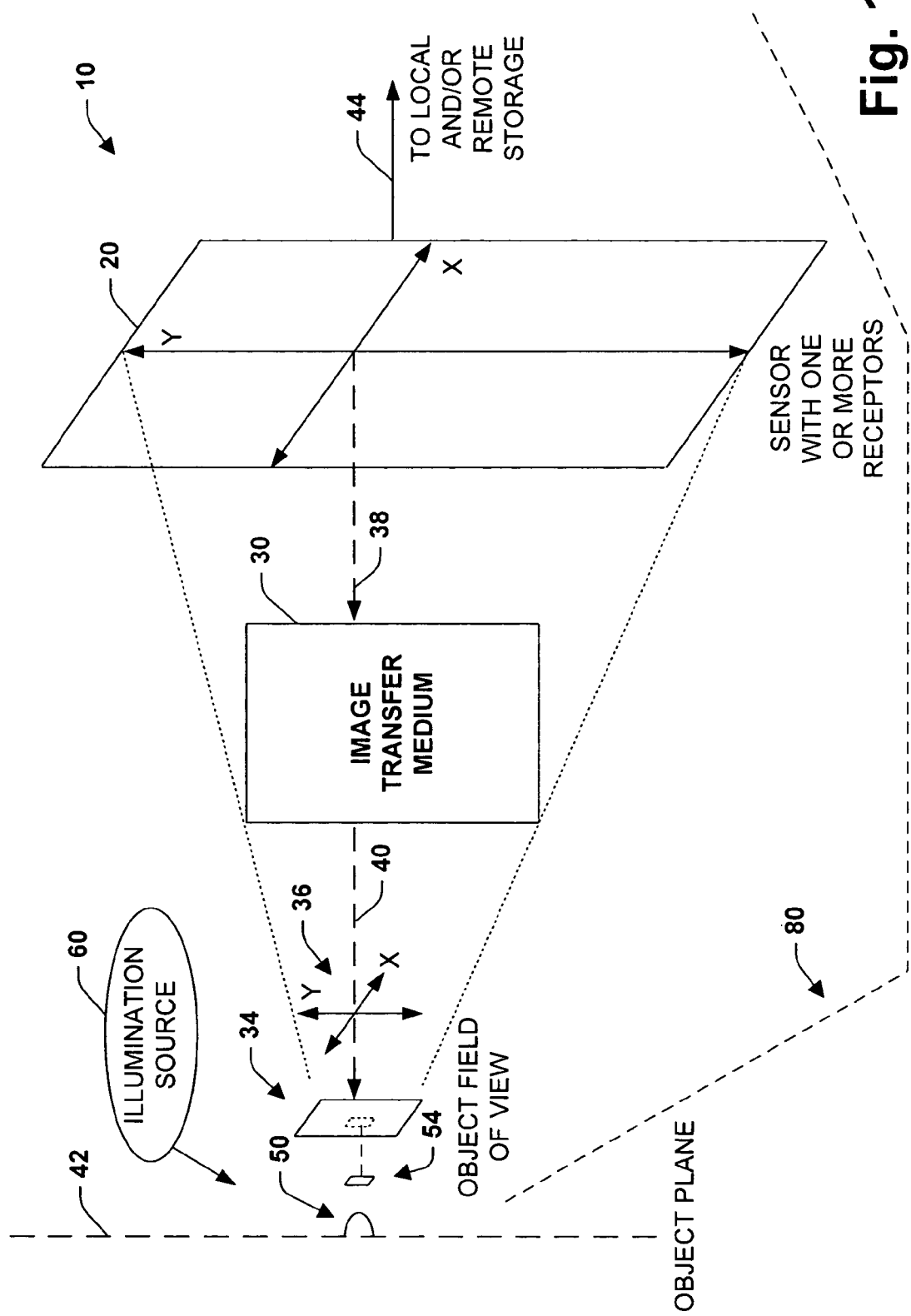
FIG. 1 is a schematic block diagram illustrating an imaging system in accordance with an aspect of the present invention.

The present invention relates to an optical and/or imaging system and methodology. According to one aspect of the present invention, a k-space filter is provided that can be configured from an image transfer medium such as optical media that correlates image sensor receptors to an optical or image transfer medium. A variety of illumination sources can also be employed to achieve one or more operational goals and for versatility of application. The k-space design of the imaging system of the present invention promotes capture and analysis (e.g., automated and/or manual) of images having a high Field Of View (FOV) at substantially high Effective Resolved Magnification as compared to conventional systems. This can include employing a small Numerical Aperture (NA) associated with lower magnification objective lenses to achieve very high Effective Resolved Magnification. As a consequence, images having a substantially large Depth Of Field (DOF) at very high Effective Resolved Magnification are also realized. The k-space design also facilitates employment of homogeneous illumination sources that are substantially insensitive to changes in position, thereby improving methods of examination and analysis.

According to another aspect of the present invention, an objective lens to object distance (e.g., Working Distance) can be maintained in operation at low and high power effective resolved magnification imaging, wherein typical spacing can be achieved at about 0.1 mm or more and about 20 mm or less, as opposed to conventional microscopic systems which can require significantly smaller (as small as 0.01 mm) object to objective lens distances for comparable (e.g., similar order of magnitude) Effective Resolved Magnification values. In another aspect, the Working Distance is about 0.5 mm or more and about 10 mm or less. It is to be appreciated that the present invention is not limited to operating at the above working distances. In many instances the above working distances are employed, however, in some instances, smaller or larger distances are employed. It is further noted that oil immersion or other Index of Refraction matching media or fluids for objective lenses are generally not required (e.g., substantially no improvement to be gained) at one or more effective image magnification levels of the present invention yet, still exceeding effective resolved magnification levels achievable in conventional microscopic optical design variations including systems employing "infinity-corrected" objective lenses.

The k-space design of the present invention defines that a small "Blur Circle" or diffraction limited point/spot at the object plane is determined by parameters of the design to match image sensor receptors or pixels with a substantially one-to-one correspondence by "unit-mapping" of object and image spaces for associated object and image fields. This enables the improved performance and capabilities of the present invention. One possible theory of the k-space design results from the mathematical concept that since the Fourier Transform of both an object and an image is formed in k-space (also called "reciprocal space"), the sensor should be mapped to the object plane in k-space via optical design techniques and component placement in accordance with the present invention. It is to be appreciated that a plurality of other transforms or models can be utilized to configure and/or select one or more components in accordance with the present invention. For example, wavelet transforms, Laplace (s-transforms), z-transforms as well as other transforms can be similarly employed.

The k-space design methodology is unlike conventional optical systems designed according to geometric, paraxial ray-trace and optimization theory, since the k-space optimization facilitates that the spectral components of the object (e.g., tissue sample, particle, semiconductor) and the image are the same in k-space, and thus quantized. Therefore, there are substantially no inherent limitations imposed on a Modulation Transfer Function (MTF) describing contrast versus resolution and absolute spatial resolution in the present invention. Quantization, for example, in k-space yields a substantially unitary Modulation Transfer Function not realized by conventional systems. It is noted that high MTF, Spatial Resolution, and effective resolved image magnification can be achieved with much lower magnification objective lenses with desirable lower Numerical Apertures (e.g., generally less than about 50× with a numerical aperture of generally less than about 0.7) through "unit-mapping" of projected pixels in an "Intrinsic Spatial Filter" provided by the k-space design.

If desired, "infinity-corrected" objectives can be employed with associated optical component and illumination, as well as spectrum varying components, polarization varying components, and/or contrast or phase varying components. These components can be included in an optical path-length between an objective and the image lens within an "infinity space". Optical system accessories and variations can thus be positioned as interchangeable modules in this geometry. The k-space design, in contrast to conventional microscopic imagers that utilize "infinity-corrected" objectives, enables the maximum optimization of the infinity space geometry by the "unit-mapping" concept. This implies that there is generally no specific limit to the number of additional components that can be inserted in the "infinity space" geometry as in conventional microscopic systems that typically specify no more than 2 additional components without optical correction.

The present invention also enables a "base-module" design that can be configured and reconfigured in operation for a plurality of different applications if necessary to employ transmissive and/or reflected illumination, if desired. This includes substantially all typical machine vision illumination schemes (e.g., darkfield, brightfield, phase-contrast), and other microscopic transmissive techniques (Kohler, Abbe), in substantially any offset and can include Epi-illumination— and variants thereof. The systems of the present invention can be employed in a plurality of opto-mechanical designs that are robust since the k-space design is substantially not sensitive to environmental and mechanical vibration and thus generally does not require heavy structural mechanical design and isolation from vibration associated with conventional microscopic imaging instruments. Other features can include digital image processing, if desired, along with storage (e.g., local database, image data transmissions to remote computers for storage/analysis) and display of the images produced in accordance with the present invention (e.g., computer display, printer, film, and other output media). Remote signal processing of image data can be provided, along with communication and display of the image data via associated data packets that are communicated over a network or other medium, for example.

Moreover, images that are created in accordance with the present invention can be stored and/or transmitted with other digital information (e.g., audio data, other images, medical histories, product information, analysis information, and so forth). For example, an image may have associated voice-encoded data describing one or more aspects of the image or images contained as part of a data package that can be stored locally and/or transmitted across a network for remote storage and/or further analysis. In one specific example, an image created in accordance with the present invention can be transmitted to a remote location, wherein the image is further analyzed (e.g., medical or product specialist analyzes received image on a computer or image display). After analysis, a voice encoding or related data is appended or encoded with the received image and then transmitted back to the originating location (or other location), wherein the image and resultant encoded analysis can be reviewed. As can be appreciated, substantially any type of digital information can be stored and/or transmitted with images that are created in accordance with the present invention.

Also, as will be apparent from the following description, the present invention can be economically implemented in a plurality of various packages including integrated imaging/computing systems that are employed to analyze various samples. Such systems include handheld devices, notebook computers, laptops, personal digital assistants, and so forth that are adapted with the imaging concepts described herein.

Referring initially to FIG. 1, an imaging system 10 is illustrated in accordance with an aspect of the present invention. The imaging system 10 includes a sensor 20 having one or more receptors such as pixels or discrete light detectors (See e.g., illustrated below in FIG. 3) operably associated with an image transfer medium 30. The image transfer medium 30 is adapted or configured to scale the proportions of the sensor 20 at an image plane established by the position of the sensor 20 to an object field of view illustrated at reference numeral 34. A planar reference 36 of X and Y coordinates is provided to illustrate the scaling or reduction of the apparent or virtual size of the sensor 20 to the object field of view 34. Direction arrows 38 and 40 illustrate the direction of reduction of the apparent size of the sensor 20 toward the object field of view 34.

The object field of view 34 established by the image transfer medium 30 is related to the position of an object plane 42 that includes one or more items under microscopic examination (not shown). It is noted that the sensor 20 can be substantially any size, shape and/or technology (e.g., digital sensor, analog sensor, Charge Coupled Device (CCD) sensor, CMOS sensor, Charge Injection Device (CID) sensor, an array sensor, a linear scan sensor) including one or more receptors of various sizes and shapes, the one or more receptors being similarly sized or proportioned on a respective sensor to be responsive to light (e.g., visible, non-visible, "light", "radiation", or other such "visible" or "invisible" or "non-visible" hereafter meaning radiation of some desired wavelength optically directed. That is: radiation of any particular wavelength whose optical path, direction, and/or path length is altered by means of an optical medium, surface, material, component, or components, or other such means suitable to radiation of that wavelength in the configuration or configurations pertaining to the direction of such radiation to achieve the desired characteristics in accordance with the present invention) received from the items under examination in the object field of view 34.

As light is received from the object field of view 34, the sensor 20 provides an output 44 that can be directed to a local or remote storage such as a memory (not shown) and displayed from the memory via a computer and associated display, for example, without substantially any intervening digital processing (e.g., straight bit map from sensor memory to display), if desired. It is noted that local or remote signal processing of the image data received from the sensor 20 can also occur. For example, the output 44 can be converted to electronic data packets and transmitted to a remote system over a network and/or via wireless transmissions systems and protocols for further analysis and/or display. Similarly, the output 44 can be stored in a local computer memory before being transmitted to a subsequent computing system for further analysis and/or display.

The scaling provided by the image transfer medium 30 is determined by a novel k-space configuration or design within the medium that promotes predetermined k-space frequencies of interest and mitigates frequencies outside the predetermined frequencies. This has the effect of a band-pass filter of the spatial frequencies within the image transfer medium 30 and notably defines the imaging system 10 in terms of resolution rather than magnification. As will be described in more detail below, the resolution of the imaging system 10 determined by the k-space design promotes a plurality of features in a displayed or stored image such as having high effective resolved magnification, high absolute spatial resolution, large depth of field, larger working distances, and a unitary Modulation Transfer Function as well as other features.

In order to determine the k-space frequencies, a "pitch" or spacing is determined between adjacent receptors on the sensor 20, the pitch related to the center-to-center distance of adjacent receptors and about the size or diameter of a single receptor. The pitch of the sensor 20 defines the Nyquist "cutoff" frequency band of the sensor. It is this frequency band that is promoted by the k-space design, whereas other frequencies are mitigated. In order to illustrate how scaling is determined in the imaging system 10, a small or diffraction limited spot or point 50 is illustrated at the object plane 42. The diffraction limited point 50 represents the smallest resolvable object determined by optical characteristics within the image transfer medium 30 and is described in more detail below. A scaled receptor 54, depicted in front of the field of view 34 for exemplary purposes, and having a size determined according to the pitch of the sensor 20, is matched or scaled to be about the same size in the object field of view 34 as the diffraction limited point 50 which is a function of the resolvable characteristics of the image transfer medium 30.

In other words, the size of any given receptor at the sensor 20 is effectively reduced in size via the image transfer medium 30 to be about the same size (or matched in size) to the size of the diffraction limited point 50. This also has the effect of filling the object field of view 34 with substantially all of the receptors of the sensor 20, the respective receptors being suitably scaled to be similar in size to the diffraction limited point 50. As will be described in more detail below, the matching/mapping of sensor characteristics to the smallest resolvable object or point within the object field of view 34 defines the imaging system 10 in terms of absolute spatial resolution and thus, enhances the operating performance of the system.

An illumination source 60 can be provided with the present invention in order that photons from the source can be transmitted through and/or reflected from objects in the field of view 34 to enable activation of the receptors in the sensor 20. It is noted that the present invention can potentially be employed without an illumination source 60 if potential self-luminous objects (e.g., fluorescent or phosphorescent biological or organic material sample, metallurgical, mineral, and/or other inorganic material and so forth) emit enough radiation to activate the sensor 60. Light Emitting Diodes, however, provide an effective illumination source 60 in accordance with the present invention. Substantially any illumination source 60 can be applied including coherent and non-coherent sources, visible and non-visible wavelengths. However, for non-visible wavelength sources, the sensor 20 and if necessary, the optical media of the image transfer medium 30 would also be suitably adapted. For example, for an infrared or ultraviolet source, an infrared or ultraviolet sensor 20 and IR or UV suitable optical components in the image transfer medium 30 would be employed, respectively. Other illumination sources 60 can include wavelength-specific lighting, broad-band lighting, continuous lighting, strobed lighting, Kohler illumination, Abbe illumination, phase-contrast illumination, darkfield illumination, brightfield illumination, and Epi illumination. Transmissive or reflective lighting techniques (e.g., specular and diffuse) can also be applied.

Reference numeral 80 depicts the outline of an image transfer medium, associated sensor, and computer system which receives image data from the associated sensor for generating images in accordance with the present invention. It is to be appreciated that these components can be configured in a plurality of different combinations such as in various portable configurations (e.g., hand held or laptop device), stand-alone configurations (e.g., industrial analyzer), or a combination of portable and stand-alone configurations/applications. For example, these configurations can include a plurality of portable imaging systems that may be powered by portable power sources, generators, batteries, solar, fuel-cell, other power sources which offer power appropriate to both the imaging system and the associated computer and display system, and can be distributed throughout differing regions to support various remote imaging applications. Such applications can include remote medicine or remote industrial applications whereby images are generated in one or more locations and transmitted to another location or location for analysis (e.g., remote pathology application, semiconductor quality control application).

Figure 2:
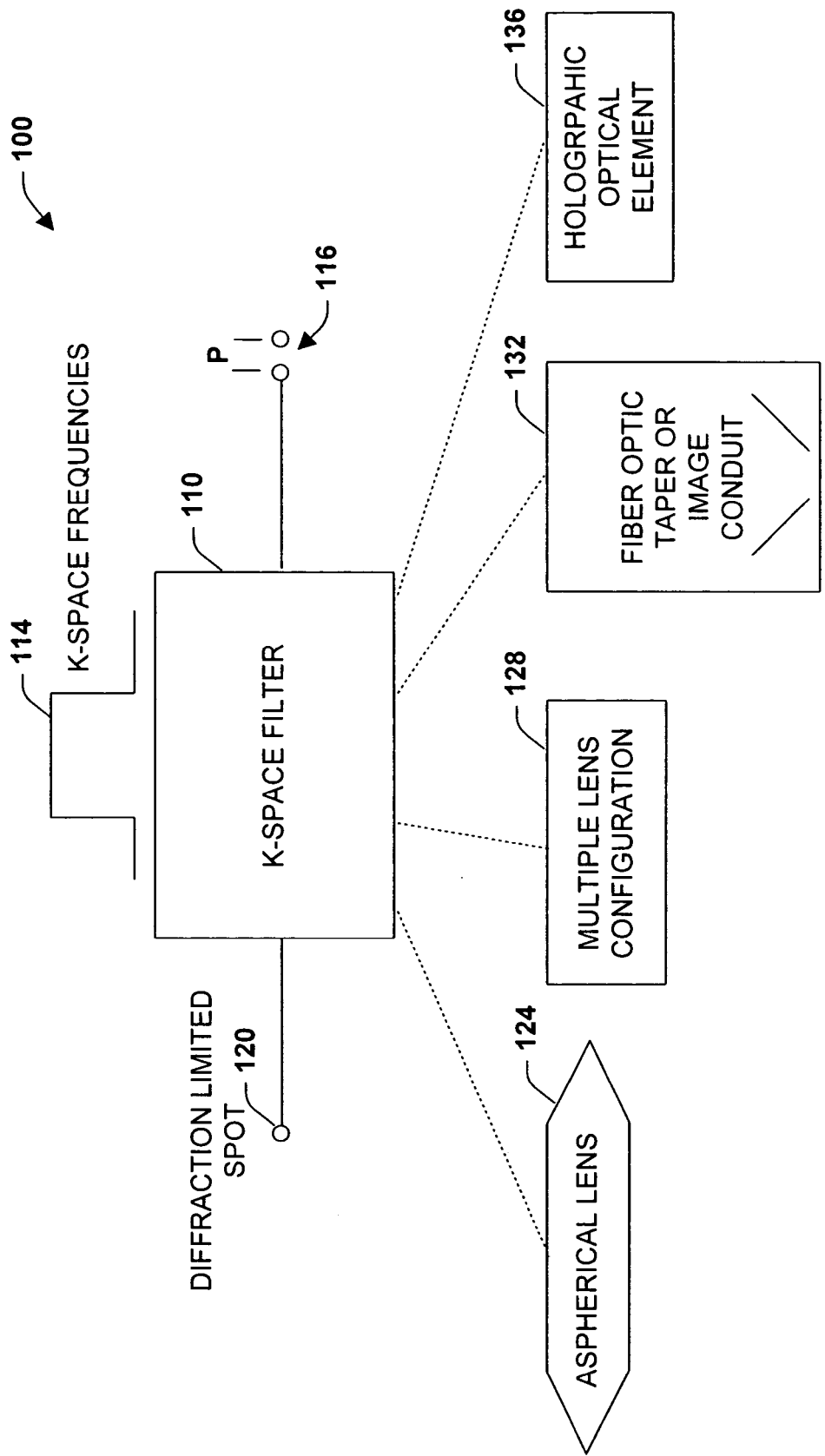
FIG. 2 is a diagram illustrating a k-space system design in accordance with an aspect of the present invention.

Referring now to FIG. 2, a system 100 illustrates an image transfer medium in accordance with an aspect of the present invention. The image transfer medium 30 depicted in FIG. 1 can be provided according to the k-space design concepts described above and more particularly via a k-space filter 110 adapted, configured and/or selected to promote a band of predetermined k-space frequencies 114 and to mitigate frequencies outside of this band. This is achieved by determining a pitch "P"—which is the distance between adjacent receptors 116 in a sensor (not shown) and sizing optical media within the filter 110 such that the pitch "P" of the receptors 116 is matched in size with a diffraction-limited spot 120. The diffraction-limited spot 120 can be determined from the optical characteristics of the media in the filter 110. For example, the Numerical Aperture of an optical medium such as a lens defines the smallest object or spot that can be resolved by the lens. The filter 110 performs a k-space transformation such that the size of the pitch is effectively matched, "unit-mapped", projected, correlated, and/or reduced to the size or scale of the diffraction limited spot 120.

It is to be appreciated that a plurality of optical configurations can be provided to achieve the k-space filter 110. One such configuration can be provided by an aspherical lens 124 adapted such to perform the k-space transformation and reduction from sensor space to object space. Yet another configuration can be provided by a multiple lens arrangement 128, wherein the lens combination is selected to provide the filtering and scaling. Still yet another configuration can employ a fiber optic taper 132 or image conduit, wherein multiple optical fibers or array of fibers are configured in a funnel-shape to perform the mapping of the sensor to the object field of view. It is noted that the fiber optic taper 132 is generally in physical contact between the sensor and the object under examination (e.g., contact with microscope slide). Another possible k-space filter 110 arrangement employs a holographic (or other diffractive or phase structure) optical element 136, wherein a substantially flat optical surface is configured via a hologram (or other diffractive or phase structure) (e.g., computer-generated, optically generated, and/or other method) to provide the mapping in accordance with the present invention.

The k-space optical design as enabled by the k-space filter 110 is based upon the "effective projected pixel-pitch" of the sensor, which is a figure derived from following ("projecting") the physical size of the sensor array elements back through the optical system to the object plane. In this manner, conjugate planes and optical transform spaces are matched to the Nyquist cut-off of the effective receptor or pixel size. This maximizes the effective resolved image magnification and the Field Of View as well as the Depth Of Field and the Absolute Spatial Resolution. Thus, a novel application of optical theory is provided that does not rely on conventional geometric optical design parameters of paraxial ray-tracing which govern conventional optics and imaging combinations. This can further be described in the following manner.

A Fourier transform of an object and an image is formed (by an optical system) in k-space (also referred to as "reciprocal-space"). It is this transform that is operated on for image optimization by the k-space design of the present invention. For example, the optical media employed in the present invention can be designed with standard, relatively non-expensive "off-the-shelf" components having a configuration which defines that the object and image space are "unit-mapped" or "unit-matched" for substantially all image and object fields. A small Blur-circle or diffraction-limited spot 120 at the object plane is defined by the design to match the pixels in the image plane (e.g., at the image sensor of choice) with substantially one-to-one correspondence and thus the Fourier transforms of pixelated arrays can be matched. This implies that, optically by design, the Blur-circle is scaled to be about the same size as the receptor or pixel pitch. The present invention is defined such that it constructs an Intrinsic Spatial Filter such as the k-space filter 110. Such a design definition and implementation enables the spectral components of both the object and the image in k-space to be about the same or quantized. This also defines that the Modulation Transfer Function (MTF) (the comparison of contrast to spatial resolution) of the sensor is matched to the MTF of the object Plane.

Figure 3:
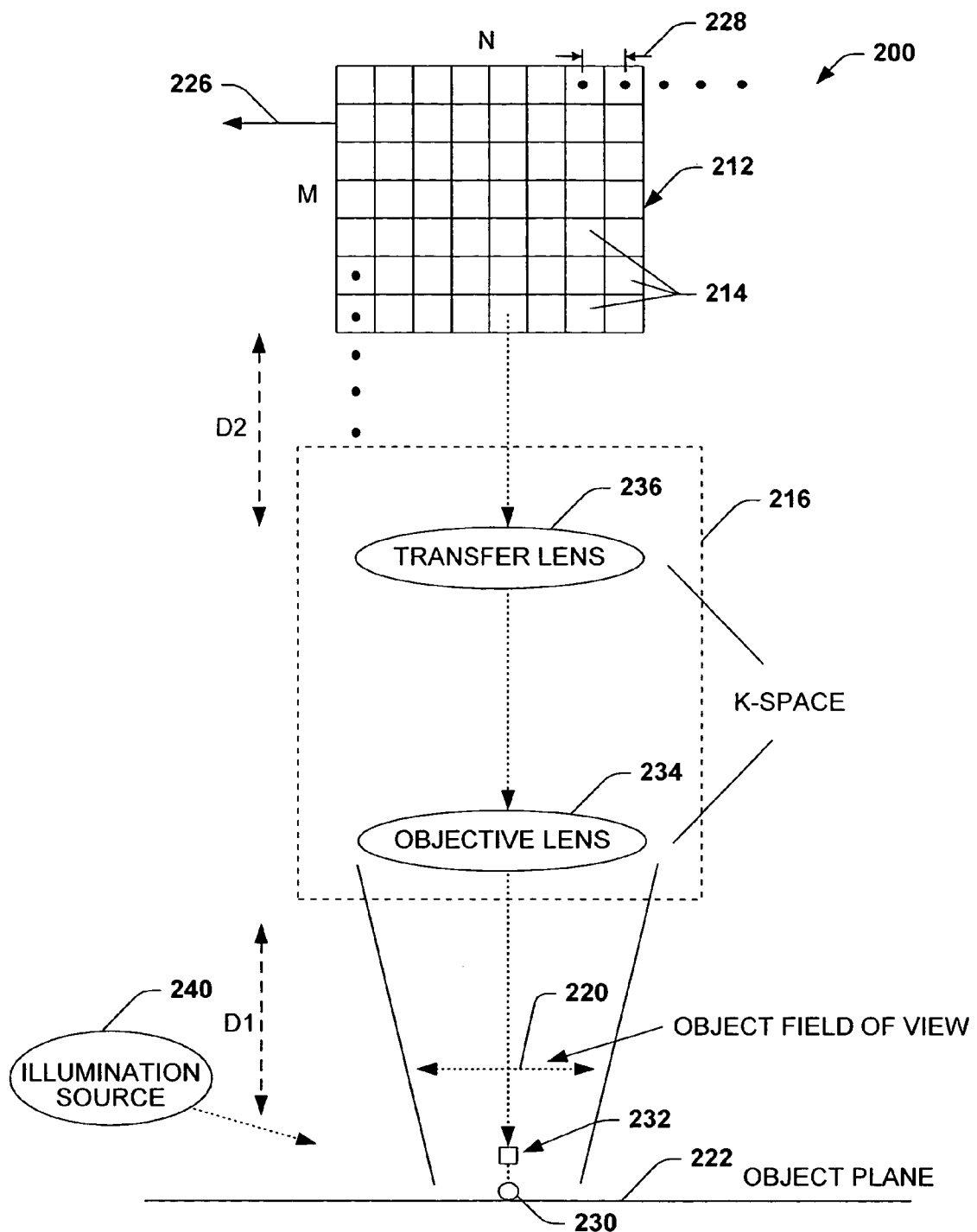
FIG. 3 is a diagram of an exemplary system illustrating sensor receptor matching in accordance with an aspect of the present invention.

FIG. 3 illustrates an optical system 200 in accordance with an aspect of the present invention. The system 200 includes a sensor 212 having a plurality of receptors or sensor pixels 214. For example, the sensor 212 is an M by N array of sensor pixels 214, having M rows and N columns (e.g., 640×480, 512×512, 1280×1024, and so forth), M and N being integers respectively. Although a rectangular sensor 212 having generally square pixels is depicted, it is to be understood and appreciated that the sensor can be substantially any shape (e.g., circular, elliptical, hexagonal, rectangular, and so forth). It is to be further appreciated that respective pixels 214 within the array can also be substantially any shape or size, the pixels in any given array 212 being similarly sized and shaped in accordance with an aspect of the present invention.

The sensor 212 can be substantially any technology (e.g., digital sensor, analog sensor, Charge Coupled Device (CCD) sensor, CMOS sensor, Charge Injection Device (CID) sensor, an array sensor, a linear scan sensor) including one or more receptors (or pixels) 214. According to one aspect of the present invention, each of the pixels 214 is similarly sized or proportioned and responsive to light (e.g., visible, non-visible) received from the items under examination, as described herein.

The sensor 212 is associated with a lens network 216, which is configured based on performance requirements of the optical system and the pitch size of sensor 212. The lens network 216 is operative to scale (or project) proportions (e.g., pixels 214) of the sensor 212 at an image plane established by the position of the sensor 212 to an object field of view 220 in accordance with an aspect of the present invention. The object field of view 220 is related to the position of an object plane 222 that includes one or more items (not shown) under examination.

As the sensor 212 receives light from the object field of view 220, the sensor 212 provides an output 226 that can be directed to a local or remote storage such as a memory (not shown) and displayed from the memory via a computer and associated display, for example, without substantially any intervening digital processing (e.g., straight bit map from sensor memory to display), if desired. It is noted that local or remote signal processing of the image data received from the sensor 212 can also occur. For example, the output 226 can be converted to electronic data packets and transmitted to a remote system over a network for further analysis and/or display. Similarly, the output 226 can be stored in a local computer memory before being transmitted to a subsequent computing system for further analysis and/or display.

The scaling (or effective projecting) of pixels 214 provided by the lens network 216 is determined by a novel k-space configuration or design in accordance with an aspect of the present invention. The k-space design of the lens network 216 promotes predetermined k-space frequencies of interest and mitigates frequencies outside the predetermined frequency band. This has the effect of a band-pass filter of the spatial frequencies within the lens network 216 and notably defines the imaging system 200 in terms of resolution rather than magnification. As will be described below, the resolution of the imaging system 200 determined by the k-space design promotes a plurality of features in a displayed or stored image, such as having high "Effective Resolved Magnification" (a figure of merit described in following), with related high absolute spatial resolution, large depth of field, larger working distances, and a unitary Modulation Transfer Function as well as other features.

In order to determine the k-space frequencies, a "pitch" or spacing 228 is determined between adjacent receptors 214 on the sensor 212. The pitch (e.g., pixel pitch) corresponds to the center-to-center distance of adjacent receptors, indicated at 228, which is about the size or diameter of a single receptor when the sensor includes all equally sized pixels. The pitch 228 defines the Nyquist "cut-off" frequency band of the sensor 212. It is this frequency band that is promoted by the k-space design, whereas other frequencies are mitigated. In order to illustrate how scaling is determined in the imaging system 200, a point 230 of a desired smallest resolvable spot size is illustrated at the object plane 222, wherein the point is derived from resolvable characteristics of the lens network 216. The point 230, for example, can represent the smallest resolvable object determined by optical characteristics of the lens network 216. That is, the lens network is configured to have optical characteristics (e.g., magnification, numerical aperture) so that respective pixels 214 are matched or scaled to be about the same size in the object field of view 220 as the desired minimum resolvable spot size of the point 230. For purposes of illustration, a scaled receptor 232 is depicted in front of the field of view 220 as having a size determined according to the pitch 228 of the sensor 212, which is about the same as the point 230.

By way of illustration, the lens network 216 is designed to effectively reduce the size of each given receptor (e.g., pixel) 214 at the sensor 212 to be about the same size (e.g., matched in size) to the size of the point 230, which is typically the minimum spot size resolvable by the system 210. It is to be understood and appreciated that the point 230 can be selected to a size representing the smallest resolvable object determined by optical characteristics within the lens network 216 as determined by diffraction rules (e.g., diffraction limited spot size). The lens network 216 thus can be designed to effectively scale each pixel 214 of the sensor 212 to any size that is equal to or greater than the diffraction limited size. For example, the resolvable spot size can be selected to provide for any desired image resolution that meets such criteria.

After the desired resolution (resolvable spot size) is selected, the lens network 216 is designed to provide the magnification to scale the pixels 214 to the object field of view 220 accordingly. This has the effect of filling the object field of view 220 with substantially all of the receptors of the sensor 212, the respective receptors being suitably scaled to be similar in size to the point 230, which corresponds to the desired resolvable spot size. The matching/mapping of sensor characteristics to the desired (e.g., smallest) resolvable object or point 230 within the object field of view 220 defines the imaging system 200 in terms of absolute spatial resolution and enhances the operating performance of the system in accordance with an aspect of the present invention.

By way of further illustration, in order to provide unit-mapping according to this example, assume that the sensor array 212 provides a pixel pitch 228 of about 10.0 microns. The lens network 216 includes an objective lens 234 and a secondary lens 236. For example, the objective lens 234 can be set at infinite conjugate to the secondary lens 236, with the spacing between the objective and secondary lenses being flexible. The lenses 234 and 236 are related to each other so as to achieve a reduction from sensor space defined at the sensor array 220 to object space defined at the object plane 222. It is noted that substantially all of the pixels 214 are projected into the object field of view 220, which is defined by the objective lens 234. For example, the respective pixels 214 are scaled through the objective lens 234 to about the dimensions of the desired minimum resolvable spot size. In this example, the desired resolution at the image plane 222 is one micron. Thus, a magnification of ten times is operative to back project a ten micron pixel to the object plane 222 and reduce it to a size of one micron.

The reduction in size of the array 212 and associated pixels 214 can be achieved by selecting the transfer lens 236 to have a focal length "D2" (from the array 212 to the transfer lens 236) of about 150 millimeters and by selecting the objective lens to have a focal length "D1" (from the objective lens 236 to the object plane 222) of about 15 millimeters, for example. In this manner, the pixels 214 are effectively reduced in size to about 1.0 micron per pixel, thus matching the size of the of the desired resolvable spot 230 and filling the object field of view 220 with a "virtually-reduced" array of pixels. It is to be understood and appreciated that other arrangements of one or more lenses can be employed to provide the desired scaling.

In view of the foregoing description, those skilled in the art will understand and appreciate that the optical media (e.g., lens network 216) can be designed, in accordance with an aspect of the present invention, with standard, relatively inexpensive "off-the-shelf" components having a configuration that defines that the object and image space are "unit-mapped" or "unit-matched" for substantially all image and object fields. The lens network 216 and, in particular the objective lens 234, performs a Fourier transform of an object and an image in k-space (also referred to as "reciprocal-space"). It is this transform that is operated on for image optimization by the k-space design of the present invention.

A small Blur-circle or Airy disk at the object plane is defined by the design to match the pixels in the image plane (e.g., at the image sensor of choice) with substantially one-to-one correspondence with the Airy disk and thus the Fourier transforms of pixilated arrays can be matched. This implies that, optically by design, the Airy disk is scaled through the lens network 216 to be about the same size as the receptor or pixel pitch. As mentioned above, the lens network 216 is defined so as to construct an Intrinsic Spatial Filter (e.g., a k-space filter). Such a design definition and implementation enables the spectral components of both the object and the image in k-space to be about the same or quantized. This also defines that a Modulation Transfer Function (MTF) (the comparison of contrast to spatial resolution) of the sensor can be matched to the MTF of the object Plane in accordance with an aspect of the present invention.

As illustrated in FIG. 3, k-space is defined as the region between the objective lens 234 and the secondary lens 236. It is to be appreciated that substantially any optical media, lens type and/or lens combination that reduces, maps and/or projects the sensor array 212 to the object field of view 220 in accordance with unit or k-space mapping as described herein is within the scope of the present invention.

To illustrate the novelty of the exemplary lens/sensor combination depicted in FIG. 3, it is noted that conventional objective lenses, sized according to conventional geometric paraxial ray techniques, are generally sized according to the magnification, Numeric Aperture, focal length and other parameters provided by the objective. Thus, the objective lens would be sized with a greater focal length than subsequent lenses that approach or are closer to the sensor (or eyepiece in conventional microscope) in order to provide magnification of small objects. This can result in magnification of the small objects at the object plane being projected as a magnified image of the objects across "portions" of the sensor and results in known detail blur (e.g., Rayleigh diffraction and other limitations in the optics), empty magnification problems, and Nyquist aliasing among other problems at the sensor. The k-space design of the present invention operates in an alternative manner to conventional geometrical paraxial ray design principles. That is, the objective lens 234 and the secondary lens 236 operate to provide a reduction in size of the sensor array 212 to the object field of view 220, as demonstrated by the relationship of the lenses.

An illumination source 240 can be provided with the present invention in order that photons from that source can be transmitted through and/or reflected from objects in the field of view 234 to enable activation of the receptors in the sensor 212. It is noted that the present invention can potentially be employed without an illumination source 240 if potential self-luminous objects (e.g., objects or specimens with emissive characteristics as previously described) emit enough radiation to activate the sensor 212. Substantially any illumination source 240 can be applied including coherent and non-coherent sources, visible and non-visible wavelengths. However, for non-visible wavelength sources, the sensor 212 would also be suitably adapted. For example, for an infrared or ultraviolet source, an infrared or ultraviolet sensor 212 would be employed, respectively. Other suitable illumination sources 240 can include wavelength-specific lighting, broad-band lighting, continuous lighting, strobed lighting, Kohler illumination, Abbe illumination, phase-contrast illumination, darkfield illumination, brightfield illumination, Epi illumination, and the like. Transmissive or reflective (e.g., specular and diffuse) lighting techniques can also be applied.

Figure 4:
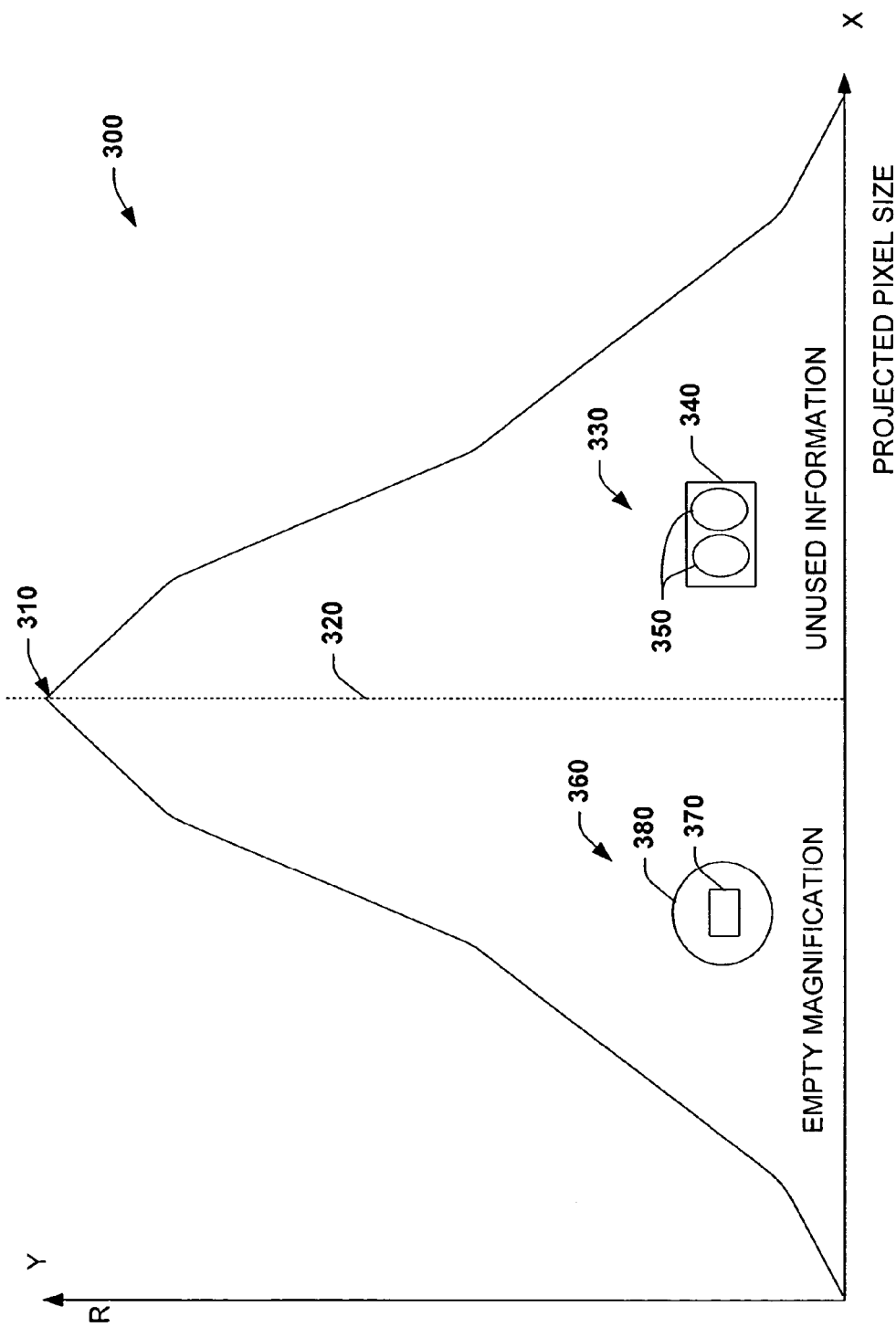
FIG. 4 is a graph illustrating sensor matching considerations in accordance with an aspect of the present invention.

FIG. 4 illustrates a graph 300 of mapping characteristics and comparison between projected pixel size on the X-axis and diffraction-limited spot resolution size "R" on the Y-axis. An apex 310 of the graph 300 corresponds to unit mapping between projected pixel size and the diffraction limited spot size, which represents an optimum relationship between a lens network and a sensor in accordance with the present invention.

It is to be appreciated that the objective lens 234 (FIG. 3) should generally not be selected such that the diffraction-limited size "R" of the smallest resolvable objects are smaller than a projected pixel size. If so, "economic waste" can occur wherein more precise information is lost (e.g., selecting an object lens more expensive than required, such as having a higher numerical aperture). This is illustrated to the right of a dividing line 320 at reference 330 depicting a projected pixel 340 larger that two smaller diffraction spots 350. In contrast, where an objective is selected with diffraction-limited performance larger than the projected pixel size, blurring and empty magnification can occur. This is illustrated to the left of line 320 at reference numeral 360, wherein a projected pixel 370 is smaller than a diffraction-limited object 380. It is to be appreciated, however, that even if substantially one-to-one correspondence is not achieved between projected pixel size and the diffraction-limited spot, a system can be configured with less than optimum matching (e.g., 0.1%, 1%, 2%, 5%, 20%, 95% down from the apex 310 on the graph 300 to the left or right of the line 320) and still provide suitable performance in accordance with an aspect of the present invention. Thus, less than optimal matching is intended to fall within the spirit and the scope of present invention.

It is further to be appreciated that the diameter of the lenses in the system as illustrated in FIG. 3, for example, should be sized such that when a Fourier Transform is performed from object space to sensor space, spatial frequencies of interest that are in the band pass region described above (e.g., frequencies utilized to define the size and shape of a pixel) are substantially not attenuated. This generally implies that larger diameter lenses (e.g., about 10 to 100 millimeters) should be selected to mitigate attenuation of the spatial frequencies of interest.

Figure 5:
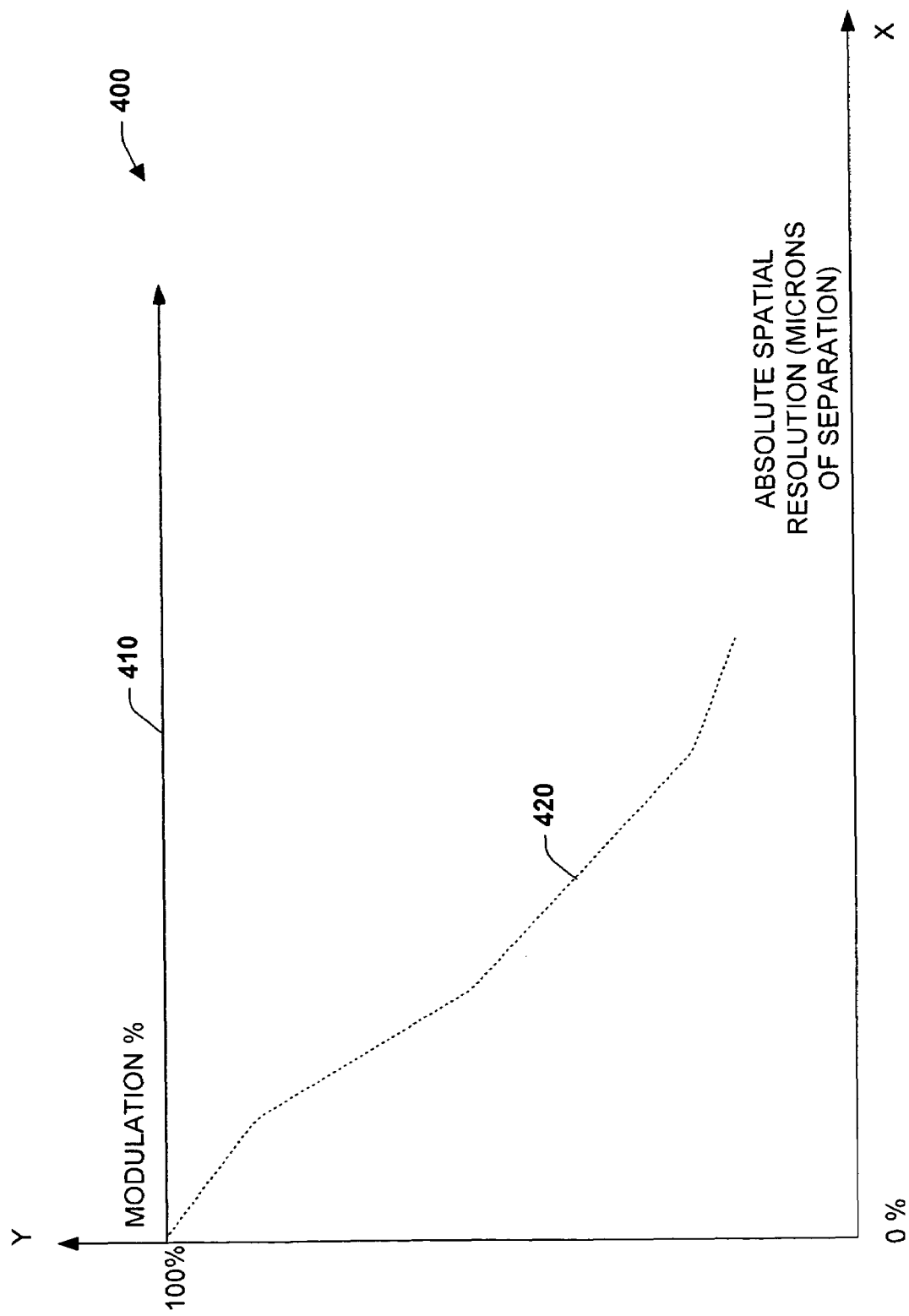
FIG. 5 is a graph illustrating a Modulation Transfer Function in accordance with an aspect of the present invention.

Referring now to FIG. 5, a Modulation Transfer function 400 is illustrated in accordance with the present invention. On a Y-axis, modulation percentage from 0 to 100% is illustrated defining percentage of contrast between black and white. On an X-axis, Absolution Spatial Resolution is illustrated in terms of microns of separation. A line 410 illustrates that modulation percentage remains substantially constant at about 100% over varying degrees of spatial resolution. Thus, the Modulation Transfer Function is about 1 for the present invention up to about a limit imposed by the signal to noise sensitivity of the sensor. For illustrative purposes, a conventional optics design Modulation Transfer Function is illustrated by line 420 which may be an exponential curve with generally asymptotic limits characterized by generally decreasing spatial resolution with decreasing modulation percentage (contrast).

Figure 6:
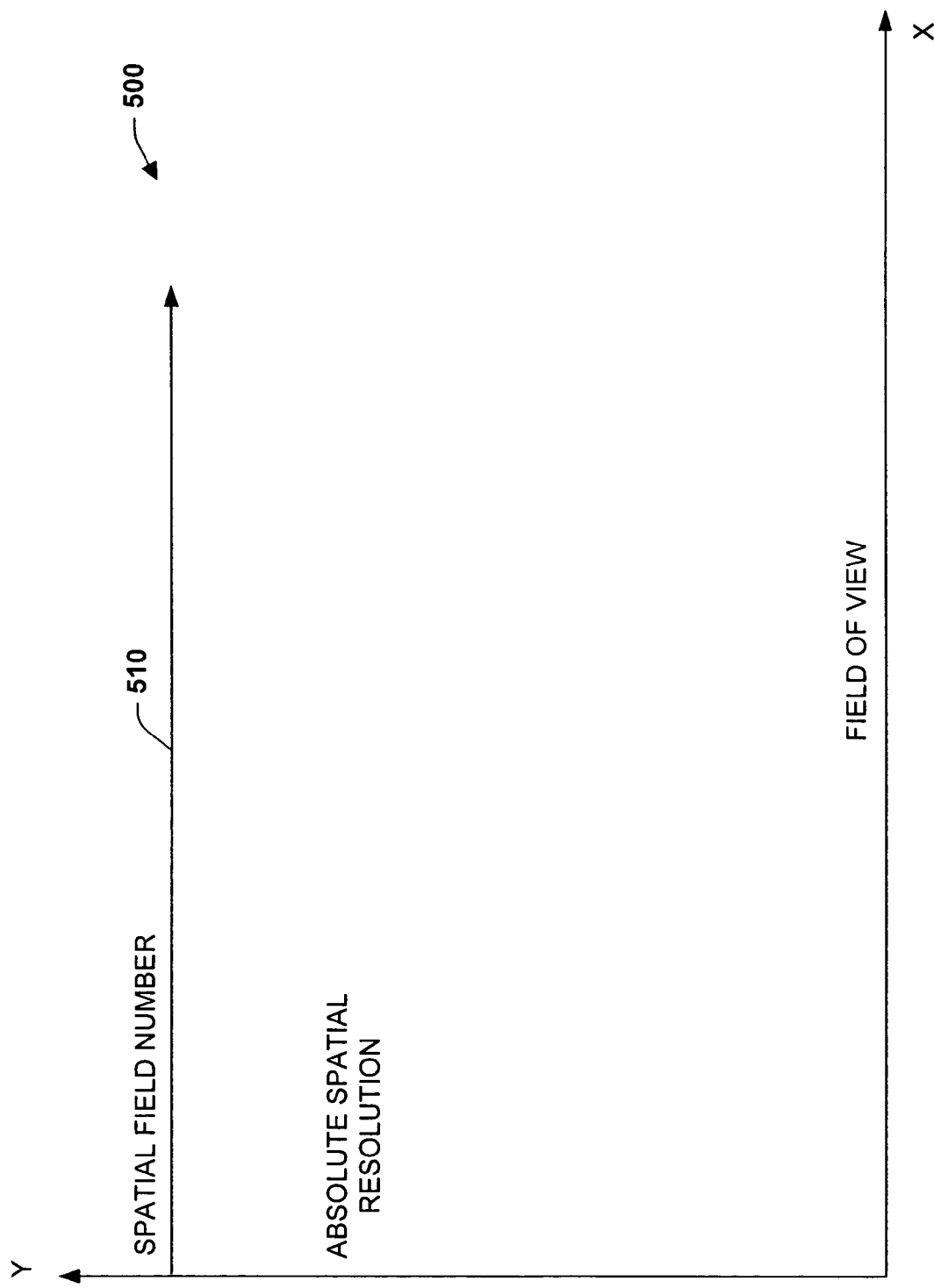
FIG. 6 is a graph illustrating a figure of merit relating to a Spatial Field Number in accordance with an aspect of the present invention.

FIG. 6 illustrates a quantifiable Figure of Merit (FOM) for the present invention defined as dependent on two primary factors: Absolute Spatial Resolution ($R_A$, in microns), depicted on the Y axis and the Field Of View (F, in microns) depicted on the X axis of a graph 500. A reasonable FOM called "Spatial Field Number" (S), can be expressed as the ratio of these two previous quantities, with higher values of S being desirable for imaging as follows:

$$S = F/R_A$$

A line 510 illustrates that the FOM remains substantially constant across the field of view and over different values of absolute spatial resolution which is an enhancement over conventional systems.

FIGS. 7, 8, 14, 15, 16, and 20 illustrate methodologies to facilitate imaging performance in accordance with the present invention. While, for purposes of simplicity of explanation, the methodologies may be shown and described as a series of acts, it is to be understood and appreciated that the present invention is not limited by the order of acts, as some acts may, in accordance with the present invention, occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the present invention.

Figure 7:
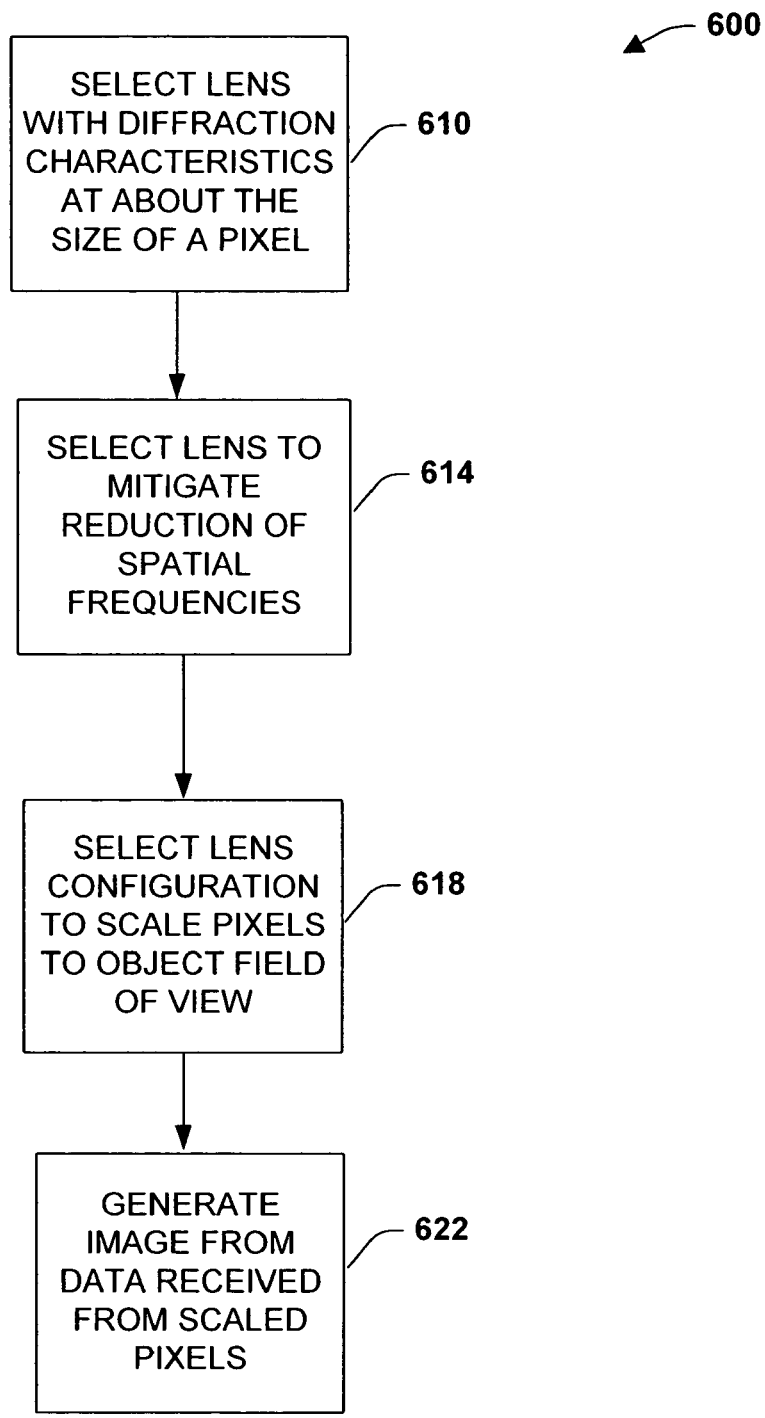
FIG. 7 is a flow diagram illustrating an imaging methodology in accordance with an aspect of the present invention.

Turning now to FIG. 7 and proceeding to 610, lenses are selected having diffraction-limited characteristics at about the same size of a pixel in order to provide unit-mapping and optimization of the k-space design. At 614, lens characteristics are also selected to mitigate reduction of spatial frequencies within k-space. As described above, this generally implies that larger diameter optics are selected in order to mitigate attenuation of desired k-space frequencies of interest. At 618, a lens configuration is selected such that pixels, having a pitch "P", at the image plane defined by the position of a sensor are scaled according to the pitch to an object field of view at about the size of a diffraction-limited spot (e.g., unit-mapped) within the object field of view. At 622, an image is generated by outputting data from a sensor for real-time monitoring and/or storing the data in memory for direct display to a computer display and/or subsequent local or remote image processing and/or analysis within the memory.

Figure 8:
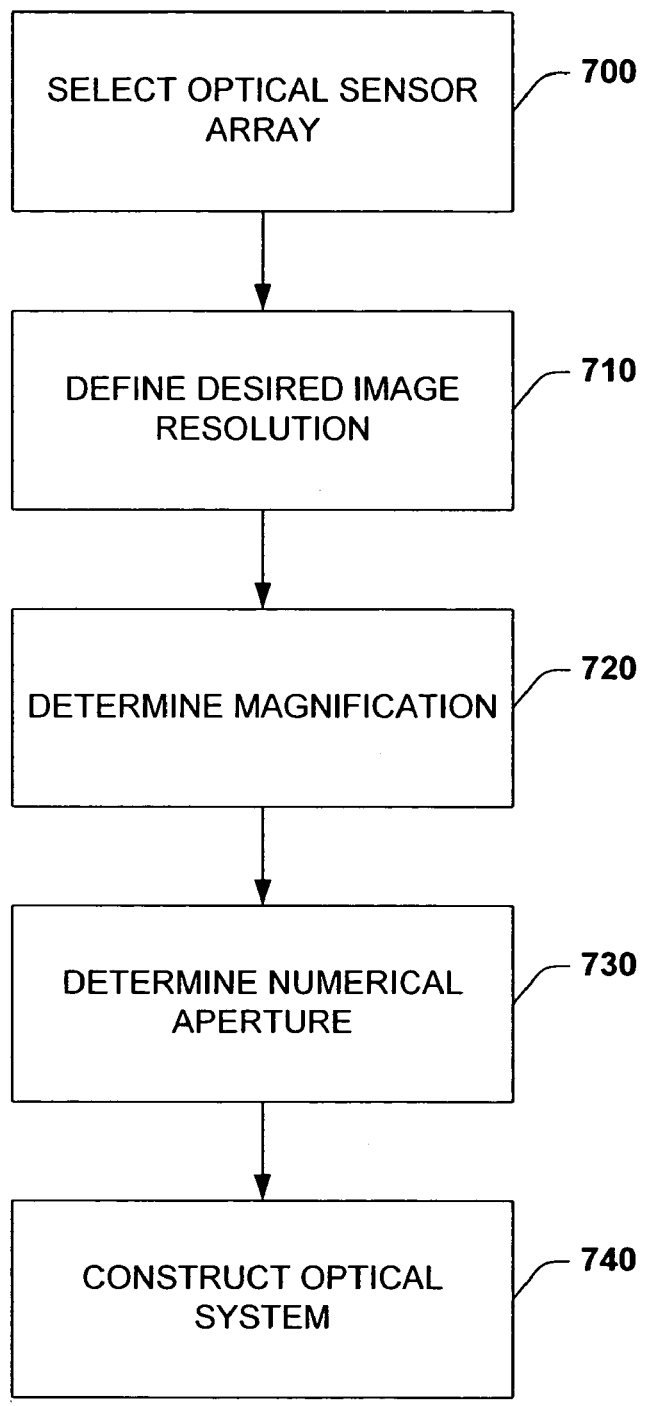
FIG. 8 is a flow diagram illustrating a methodology for selecting optical parameters in accordance with an aspect of the present invention.

FIG. 8 illustrates a methodology that can be employed to design an optical/imaging system in accordance with an aspect of the present invention. The methodology begins at 700 in which a suitable sensor array is chosen for the system. The sensor array includes a matrix of receptor pixels having a known pitch size, usually defined by the manufacturer. The sensor can be substantially any shape (e.g., rectangular, circular, square, triangular, and so forth). By way of illustration, assume that a sensor of 640×480 pixels having a pitch size of 10 μm is chosen. It is to be understood and appreciated that an optical system can be designed for any type and/or size of sensor array in accordance with an aspect of the present invention.

Next at 710, an image resolution is defined. The image resolution corresponds to the smallest desired resolvable spot size at the image plane. The image resolution can be defined based on the application(s) for which the optical system is being designed, such as any resolution that is greater than or equal to a smallest diffraction limited size. Thus, it is to be appreciated that resolution becomes a selectable design parameter that can be tailored to provide desired image resolution for virtually any type of application. In contrast, most conventional systems tend to limit resolution according to Rayleigh diffraction, which provides that intrinsic spatial resolution of the lenses cannot exceed limits of diffraction for a given wavelength.

After selecting a desired resolution (710), a suitable amount of magnification is determined at 720 to achieve such resolution. For example, the magnification is functionally related to the pixel pitch of the sensor array and the smallest resolvable spot size. The magnification (M) can be expressed as follows:

$$M = \frac{x}{y} \qquad \text{Eq. 1}$$

wherein: x is the pixel pitch of the sensor array; and
y is the desired image resolution (minimum spot size).

So, for the above example where the pixel pitch is 10 μm and assuming a desired image resolution of 1 μm, Eq. 1 provides an optical system of power ten. That is, the lens system is configured to back-project each 10 μm pixel to the object plane and reduce respective pixels to the resolvable spot size of 1 micron.

The methodology of FIG. 8 also includes a determination of a Numerical Aperture at 730. The Numerical Aperture (NA) is determined according to well-established diffraction rules that relate NA of the objective lens to the minimum resolvable spot size determined at 710 for the optical system. By way of example, the calculation of NA can be based on the following equation:

$$NA = \frac{0.5 \times \lambda}{y} \qquad \text{Eq. 2}$$

where: $\lambda$ is the wavelength of light being used in the optical system; and
y is the minimum spot size (e.g., determined at 710).

Continuing with the example in which the optical system has a resolved spot size of y =1 micron, and assuming a wavelength of about 500 nm (e.g., green light), a NA=0.25 satisfies Eq. 2. It is noted that relatively inexpensive commercially available objectives of power 10 provide numerical apertures of 0.25.

It is to be understood and appreciated that the relationship between NA, wavelength and resolution represented by Eq. 2 can be expressed in different ways according to various factors that account for the behavior of objectives and condensers. Thus, the determination at 730, in accordance with an aspect of the present invention, is not limited to any particular equation but instead simply obeys known general physical laws in which NA is functionally related to the wavelength and resolution. After the lens parameters have been designed according to the selected sensor (700), the corresponding optical components can be arranged to provide an optical system (740) in accordance with an aspect of the present invention.

Assume, for purposes of illustration, that the example optical system created according to the methodology of FIG. 8 is to be employed for microscopic-digital imaging. By way of comparison, in classical microscopy, in order to image and resolve structures of a size approaching 1 micron (and below), magnifications of many hundreds usually are required. The basic reason for this is that such optics conventionally have been designed for the situation when the sensor of choice is the human eye. In contrast, the methodology of FIG. 8 designs the optical system in view of the sensor, which affords significant performance increases at reduced cost.

In the k-space design methodology, according to an aspect of the present invention, the optical system is designed around a discrete sensor that has known fixed dimensions. As a result, the methodology can provide a far more straight-forward, robust, and inexpensive optical system design approach to "back-project" the sensor size onto the object plane and calculate a magnification factor. A second part of the methodology facilitates that the optics that provide the magnification have a sufficient NA to optically resolve a spot of similar dimensions as the back-projected pixel. Advantageously, an optical system designed in accordance with an aspect of the present invention can utilize custom and/or off-the-shelf components. Thus, for this example, inexpensive optics can be employed in accordance with an aspect of the present invention to obtain suitable results, but well-corrected microscope optics are relatively inexpensive. If custom-designed optics are utilized, in accordance with an aspect of the present invention, then the range of permissible magnifications and numerical apertures becomes substantial, and some performance gains can be realized over the use of off-the-shelf optical components.

In view of the concepts described above in relation to FIGS. 1-8, a plurality of related imaging applications can be enabled and enhanced by the present invention. For example, these applications can include but are not limited to imaging, control, inspection, microscopy and/or other automated analysis such as:

(1) Bio-medical analysis (e.g., cell colony counting, histology, frozen sections, cellular cytology, Mechanical, Laser or radiation-based, and other Micro-dissection, Hematology, pathology, oncology, fluorescence, interference, phase and many other clinical microscopy applications);

(2) Particle Sizing Applications (e.g., Pharmaceutical manufacturers, paint manufacturers, cosmetics manufacturers, food process engineering, and others);

(3) Air quality monitoring and airborne particulate measurement (e.g., clean room certification, environmental certification, and so forth);

(4) Optical defect analysis, and other requirements for high resolution microscopic inspection of both transmissive and opaque materials (as in metallurgy, automated semiconductor inspection and analysis, automated vision systems, 3-D imaging and so forth); and (5) Imaging technologies such as cameras, copiers, FAX machines and medical systems as well as other technologies/applications which are described in more detail below.

FIGS. 9-16 illustrate possible example systems that can be constructed employing the concepts previously described above in relation to FIGS. 1-8.

Figure 9:
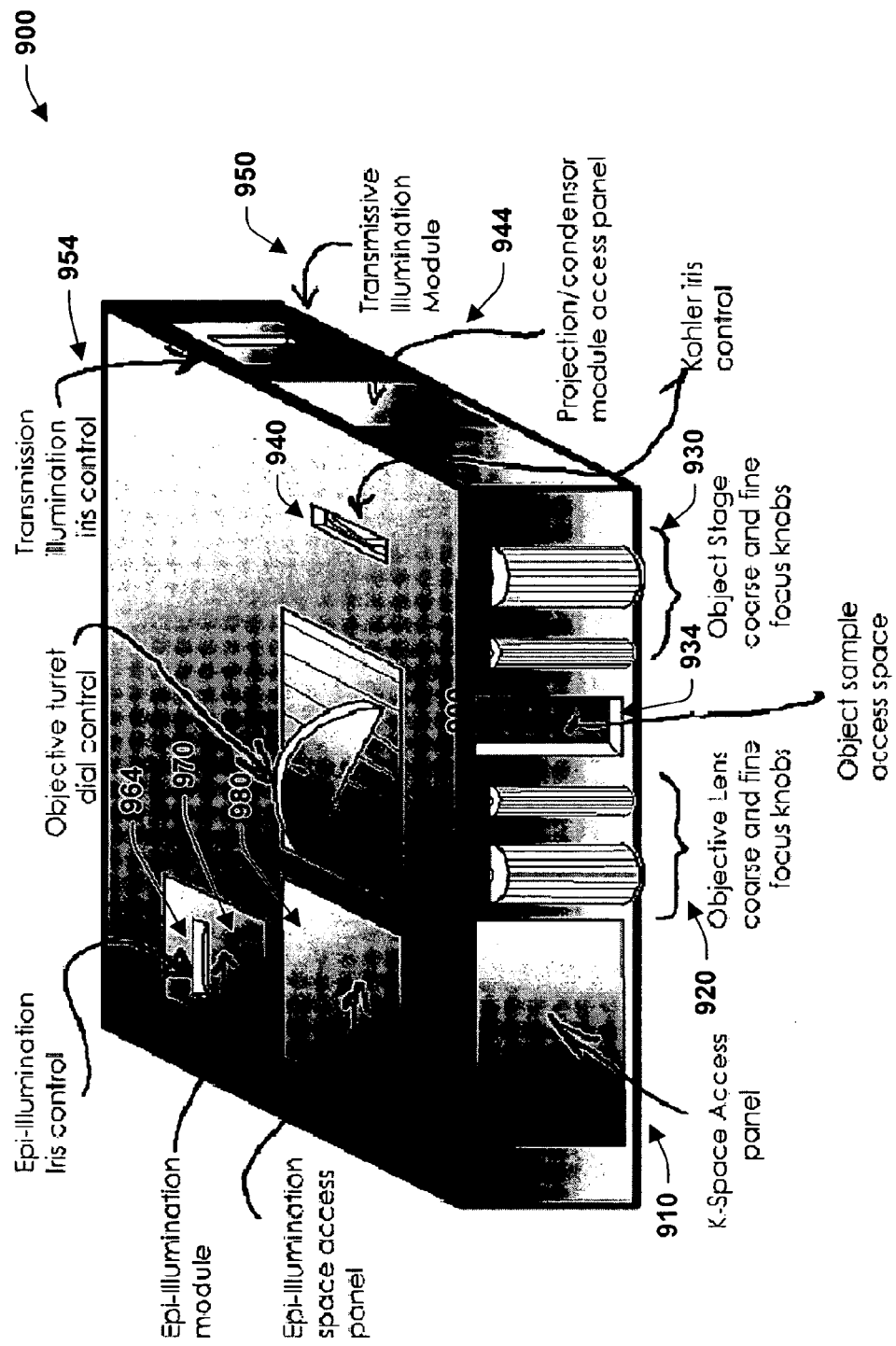
FIGS. 9-16 illustrate various exemplary imaging designs in accordance with an aspect of the present invention.

FIG. 9 depicts an example packaging concept and system 900 for an imaging system adapted in accordance with the present invention. In this aspect, the system 900 includes imaging components such as a sensors, optics, and adjustments that provide imaging data to an associated computer (not shown) through substantially any desired coupling technique such as a Firewire, USB port, parallel port, infrared, and so forth. It is to be appreciated however, that a computer system (or portions thereof, e.g., memory components) could be provided within the system 900.

The system 900 can include such aspects as a k-space access panel at 910, various adjustment devices 920 and 930 for adjusting or positioning lenses and/or stages for viewing desired objects, and one or more access spaces 934 to insert an object sample. These adjustments, as well as sample ingress, egress, and handling, can be automated such as via servo controls, manual controls, or combinations of manual and automatic controls. Other features of the system 900 include Koehler iris controls 940, a projection/condensor access panel 944, and a transmissive illumination module 950 having an associated transmission illumination iris control 954. Other controls include an objective turret dial control 960 and an EPI-illumination control 964 associated with an Epi-illumination module 970. An Epi-Illumination access space 980 can also be provided.

Figure 10:
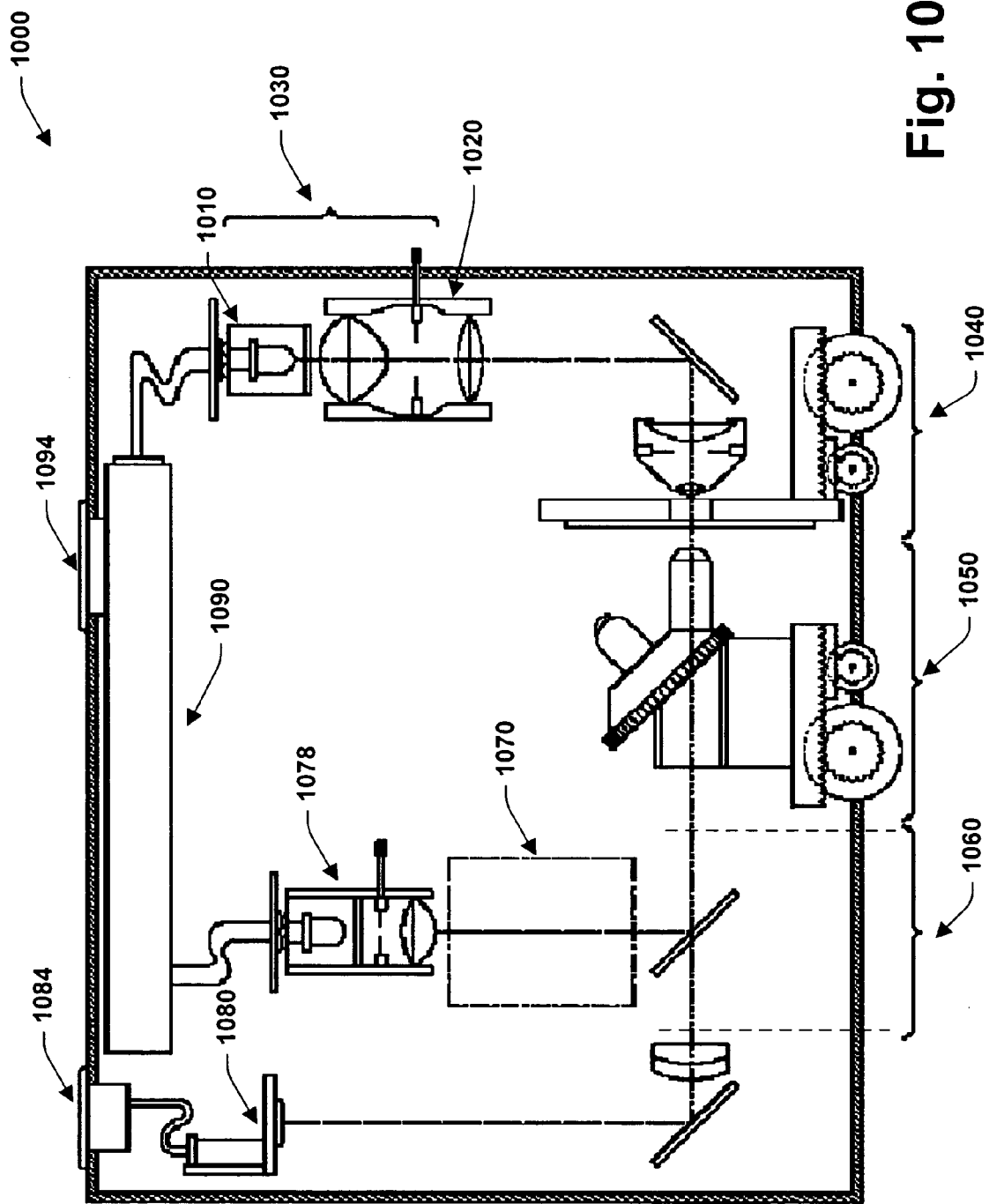

FIG. 10 depicts a system assembly layout 1000 for the system 900 illustrated in FIG. 9, wherein such system can be configured in a hand held or portable arrangement (e.g., 10 inches by 12 inches apparent footprint). At 1010, an LED solid-state illumination source having an associated holographic/diffractive optical element is provided. At 1020, a projection condensor module is provided. At 1030, an illumination module assembly is provided. At 1040, a Koehler/Abbe microscope condenser and stage assembly is provided, each of the which may have axially moveable components for object focus. At 1050, turret mounted objective lenses are provided that can be axially moveable and lockable for object field of view focus. It is to be appreciated that such multiple objective configurations may include as many or few lenses as is practicable or desirable in any chosen design configuration. Also, rather than a turret, a linear slide configuration of lenses can be provided.

At 1060, a k-space access section is provided. At 1070, an optical path for filters and/or other optical components is provided. At 1078, an Epi-illumination assembly is provided having an associated holographic/diffractive optical element. It is noted that any of the light sources described herein can be adapted or changed for various different wavelengths. Also, different types of sources can be provided. For example, in certain low power applications, a conventional LED (having differing wavelengths) can be employed, whereas for other applications, a light source such as a Luxeon star can be employed. At 1080 a sensor detector module and access entry is provided. At 1084, a detector connector for sending image data to a computer is provided. At 1090, an exemplary battery/power module is provided and an AC or other power input can be provided at 1094.

Figure 11:
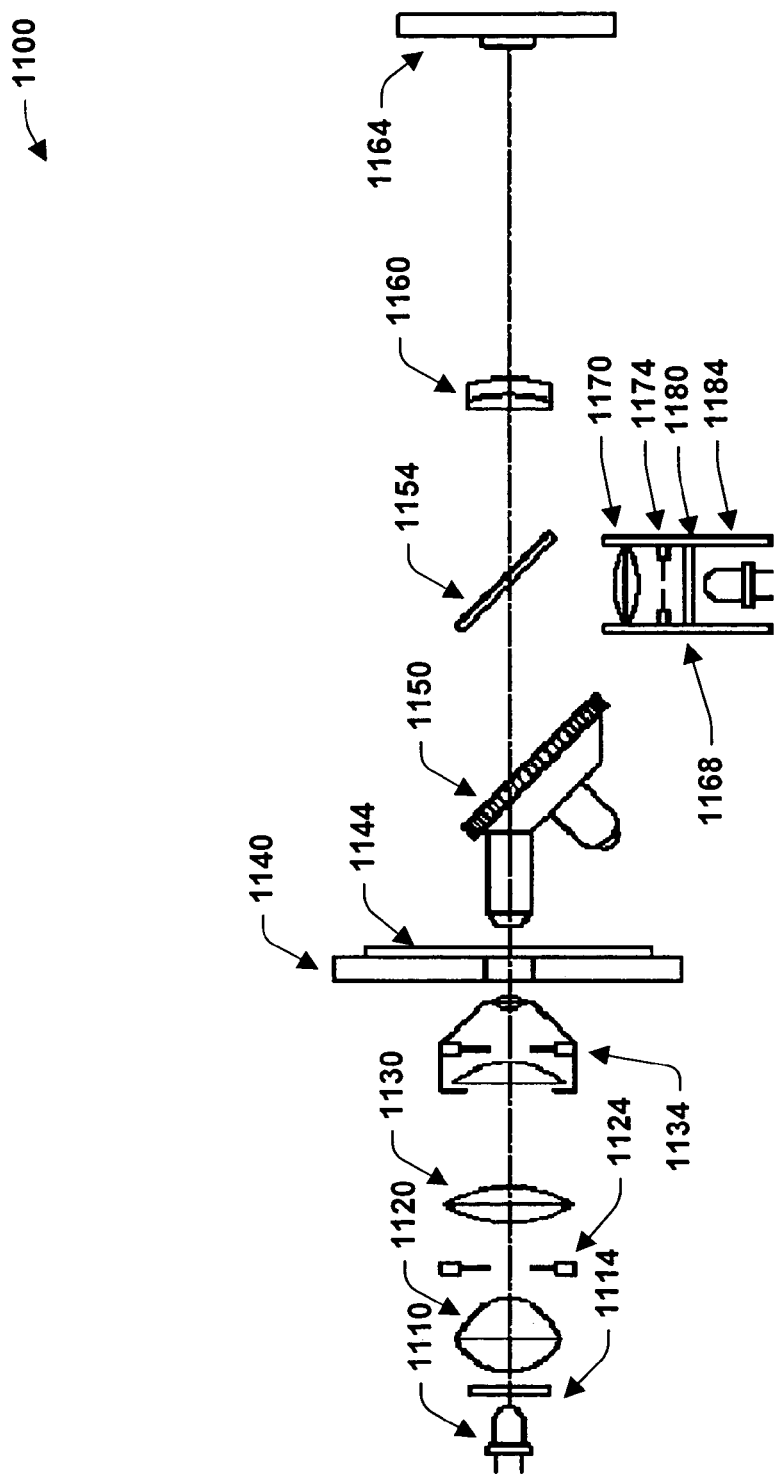

FIG. 11 illustrates an optical train assembly 1100 in accordance with an aspect of the present invention. The assembly 1100 includes one or more of the following: an illumination source 1110, a holographic/diffractive optical element 1114, a condenser projection lens 1120 (generally aspheric), an iris diaphragm or aperture 1124, a field lens 1130, a Kohler or Abbe microscope condensor 1034, a moveable stage assembly 1140, a sample 1144 (e.g., transparent or opaque sample or slide), turret mounted microscope objectives 1150 (axially moveable and lockable for object Field of View focus), a beam splitter 1154, a telan or tube or field lens 1160, a detector system 1164 (CMOS, CCD, and so forth), an EPI illumination assembly 1168 having a projection lens 1170, an iris diaphragm/aperture 1174, a holographic/diffractive optical element 1180, and an illumination source 1184 (wavelength selectable devices).

Figure 12:
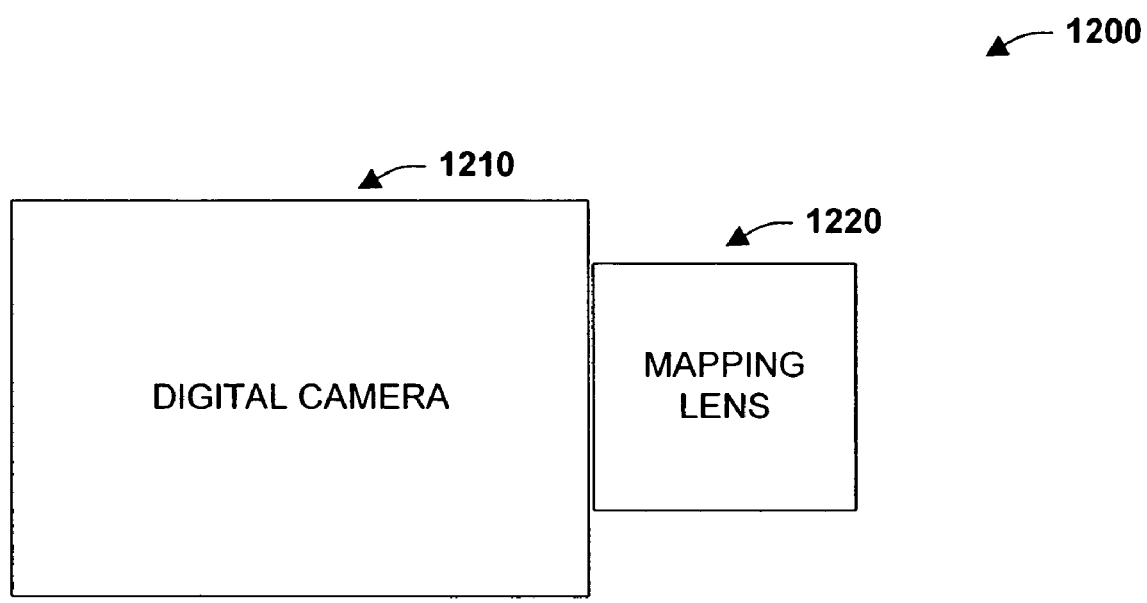

FIG. 12 illustrates an alternative portable imaging and microscope device 1200 in accordance with an aspect of the present invention. In this aspect, a digital camera 1210 is adapted with a mapping lens 1220 (or lens assembly) to provide a hand held microscopic imaging device. The mapping lens 1220 provides projected pixel mapping or correlation between the camera sensor and a diffraction-limited spot defined by the lens. It is noted that in one example of a medical imager, by using numbers (below), approximately 1.75×1.32 millimeters of object can be imaged by the camera 1210—yielding approximately 25 pixels per red cell, and 100-500 pixels per white cell, at a resolution of 1 micron, for example. A hematology analysis can proceed with 1,000 cells (total), thus a single image will be capable of holding sufficient information for a full cell count. In an example design the following may apply:

1. select a desired resolution, e.g., 1 micron.
2. calculate that the objective lens would need an NA of approximately 0.3 based on example resolution of 1 micron.
3. calculate that the magnification required to get from 1 micron of resolution to 5.4 microns of pixel-quadrad pitch is approximately 5×
4. construct a k-space-transfer microscope with a 5×NA=0.3 objective lens
5. employ a digital camera (e.g., Sony DSC-F828), remove the lens sold with camera, and mate the camera to the k-space microscope described in 4.

In general, "desired" is what a CCD sensor (or other type) is capable of, wherein "3-filter" is what current CCDs perform (usually RGGB quadrads of pixels) and "4-filter" such as Sony performs (RGBC quadrad). Other non-rectangular geometries can also be employed, such as hexagonal or pentagonal, whereby more filters can be adapted on the extra pixels to further fill-in the colors currently missed by a 3-filter arrangement.

FIGS. 13-16 describe another exemplary portable system in accordance with the present invention. In general, in nearly all cases whereby a digital sensor is attached to an imaging system capable of high effective magnification, the resulting system is non-portable due to constraints of size, required power, and support infrastructure. One of the main considerations is that conventional systems are designed for human use, and do not take advantage of the inherent possibilities of a discrete sensor approach.

When an imaging system is designed to take full advantage of the properties of a discrete sensor array, many of the design parameters that have to be considered for a conventional system can be discarded, leading to a greatly simplified system which exhibits a similar (or better) effective magnification, similar (or better) resolution, and much lower light requirements.

As an example of a reduced-size system, the following describes a fully-integrated hematology system (or other application) which has direct relevance to emerging (third-world) countries where a simple, fast blood analysis (e.g., HIV, sickle-cell anemia) would be of great value.

Some considerations are that the system should be capable of being powered from a variety of sources (battery, line voltage, solar cell), should have a minimum of moving parts, and should have robust software (i.e., embedded firmware). In addition, the system cost should be minimal. Also, the system should be capable of performing all commonly utilized tests that involve samples as presented to a microscope on a slide substrate.

The following describes some possible considerations:
sensor considerations:
  the sensor should be heavily integrated and not require complex support circuitry
  the sensor should require very little power
  the sensor should be sensitive to low levels of light
  the sensor should have a wide dynamic range
  the sensor should have a large number of active sites (pixels) but not be so large as to require excessive data transfer times (i.e., 1 k×1 k array)
optical considerations:
  the system should conform to k-space design parameters
  the system should have as wide a field of view as practical
  the system should be as near to focus-free as practical
  the system should have a large depth of field
  the system should use simple optical components
lighting considerations:
  should have low power requirements
  should require minimal user adjustment
  should have extended life
mechanical considerations
  the system should be very robust to allow for field-usage
  the system should allow easy field-servicing
  the system should be as modular as possible
  the system should be light to allow for portability
digital considerations
  computing power is not a necessity, so a moderately low-performance computing platform will suffice
  very low electrical power consumption
  common computing functions should be integrated onto the main computing platform
  outputs for LCD and CRT should be provided for flexibility
  provision for external storage for any presently extant or future storage media should be made, with interfaces for floppy disk, memory stick, USB memory adapter, printer, CDROM, DVDROM, and/or hard disk
  basic computing functions, such as the operating system and application software should be embedded in non-volatile storage such as ROM or flash memory, leading to diskless operation
  the OS and application software should be robust and capable of extension either on-site by the user, or remotely by e.g., dialup or wireless internet connection.

Figure 13:
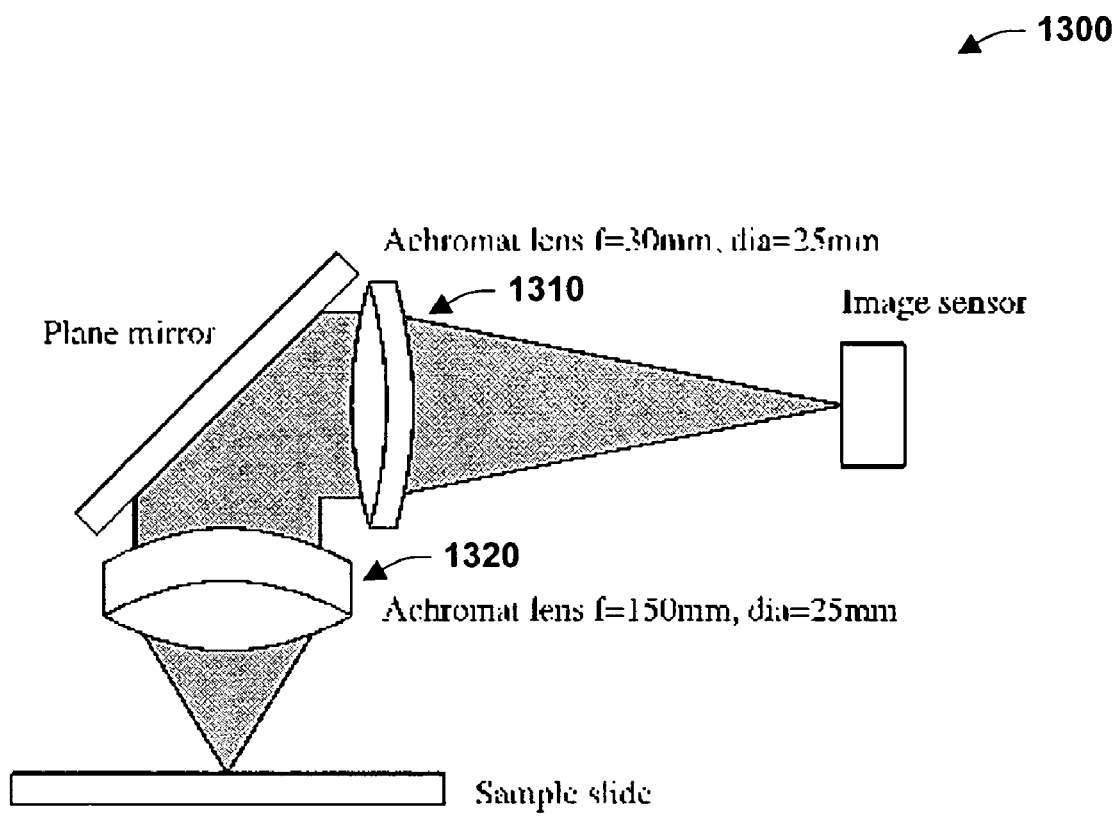

One example implementation of the above system:
sensor:
  a CMOS array with the above-described characteristics, and is available in sizes from 640×480 to 1280×1024 with pixels of approximately 5 microns.
  typical power requirements are in the low 10's of milliwatts.
optics as depicted in the optical configuration 1300 of FIG. 13:
  for a hematology analysis system, a base resolution of one micron per pixel is quite sufficient to resolve and identify red cells (5 um) and white cells (25 um).
  referring to the proposed CMOS sensor, this leads to an optical magnification of 5× requirement to map a single pixel onto the object plane with a resolution of 1 um.
  for a magnification of 5×, and a projected pixel-pitch of 1 um, the required Numerical Aperture of the imaging lens to provide a diffraction-limited 1 um spot is 0.25.
  for such modest magnification requirements, the optical design can be met using a simple Gauss-pair of achromats 1310 and 1320. The optimal design would use a sensor lens of focus f=150 mm, diameter d=25 mm an imaging lens of f=30 mm, d=25 mm (giving an NA of slightly greater than 0.25)
  referring to an example 1280×1024 pixel sensor and the above optical prescription, an imaging system is provided capable of 1 um resolution with a field of view of 1.2 mm×1 mm, and depth of focus (field) approaching 10 microns.

Figure 14:
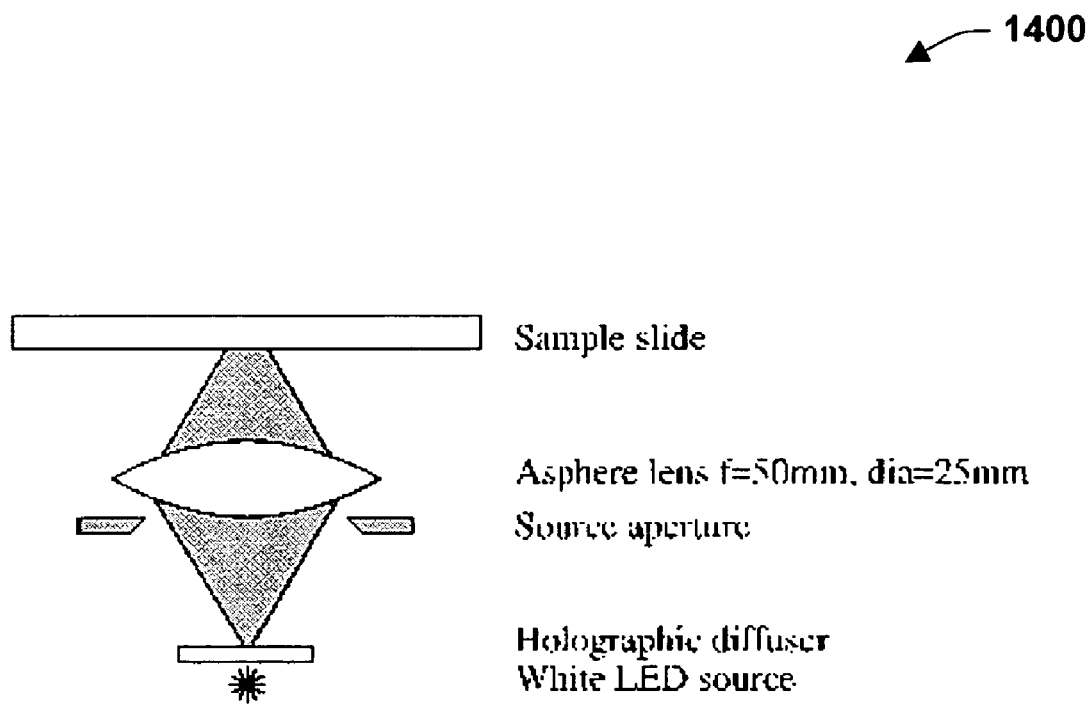
Figure 15:
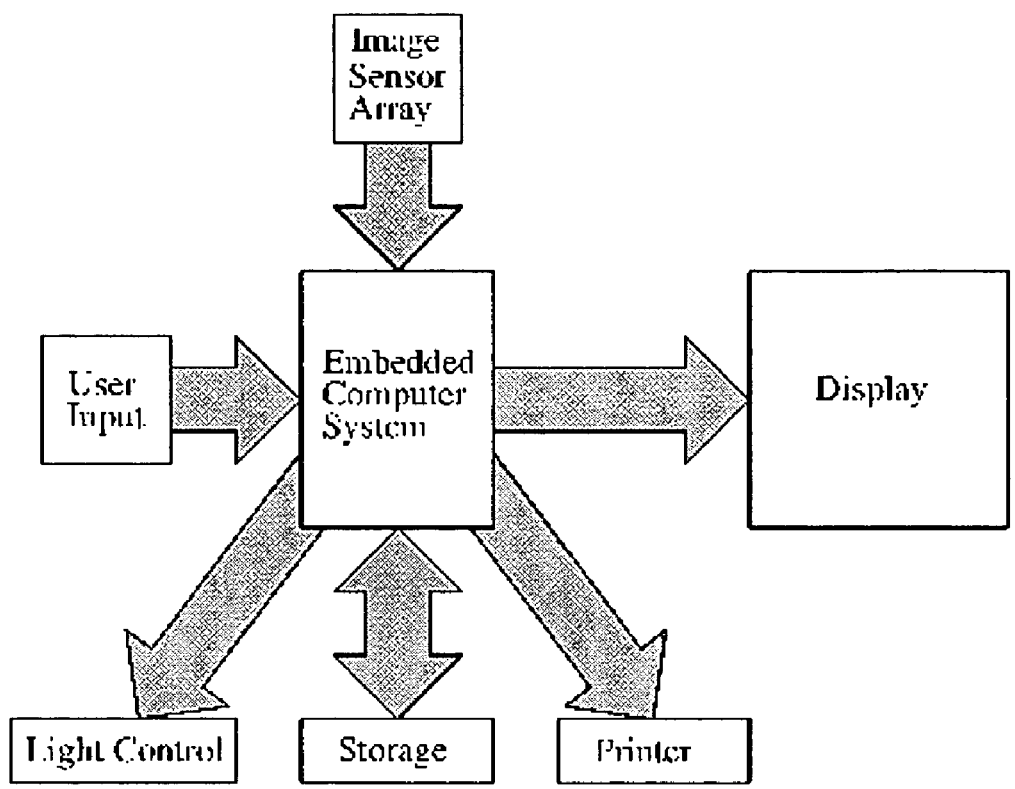

FIG. 14 illustrates a lighting system 1400 having possible parameters as follows:
  white LEDs should be used with consequently low power requirements (<50 mW) and long operating life (50,000+hours)
  light homogenisation via holographic diffusers should be used (leading to a virtual point-source)
  Kohler sub-stage (transmissive) lighting should be provided
  option should be made for white-light or UV epi-illumination if required.
optomechanics
  components should be standard sizes (e.g. 25 mm/1 inch diameter)
  components should be corrosion-resistant (due to the commonly-met chemical environment in haematology)
  all components should be easily assembled in the form of modules
  e.g., components from Thorlabs, Linos and similar FIG. 15 illustrates an example processing system 1500 having possible configurations of:
  the processor of can be an ARM range (Advanced RISC Machines or other type), which are widely accepted as having the best performance to power ratio. Additionally, many of the ARM variants are available as "system on chip" designs, where a CPU, FPU, IO and Video subsystems are fully integrated into a single-chip package (e.g., ARM 7500 FE, StrongARM 1110)
  the operating system can be a RISCOS (or other type), which is a ROM-based OS that has both high- and low-level abstractions, is very robust, and has been deployed since 1987. It also has a very simple and intuitive graphical user interface. Code density, due to the RISC techniques employed, is very good, and major applications generally only use 100's of kilobytes.
  typically, complete computing systems can be obtained that make use of RISCOS and the ARM processors in the form of single-board computers. Power requirements very rarely exceed 5-10 Watts. On-board storage is typically supplied in the form of flash memory (16-64 megabytes). Common sizes for the computer boards are 100 mm×150 mm, and this has lead to the availability of low-power LCD displays with integrated computer boards (e.g., Explan SOLO, Castle SLYM)
  for a completely integrated haematology solution (or other application), direct interfacing of the sensor array into the main memory space of the host computer avoids complications and expense consequent with standard interfaces (e.g., USB, IEEE-1394), and also allows simple control of the sensor functions. Some sophistication can be achieved by using double-buffered memory (e.g., VRAM) to act as an arbitrator between the sensor and the host CPU.

for the above-described system, power requirements generally fall within a 10 watt power budget, and can be met by battery, line, or solar-cell supplies.

Figure 16:
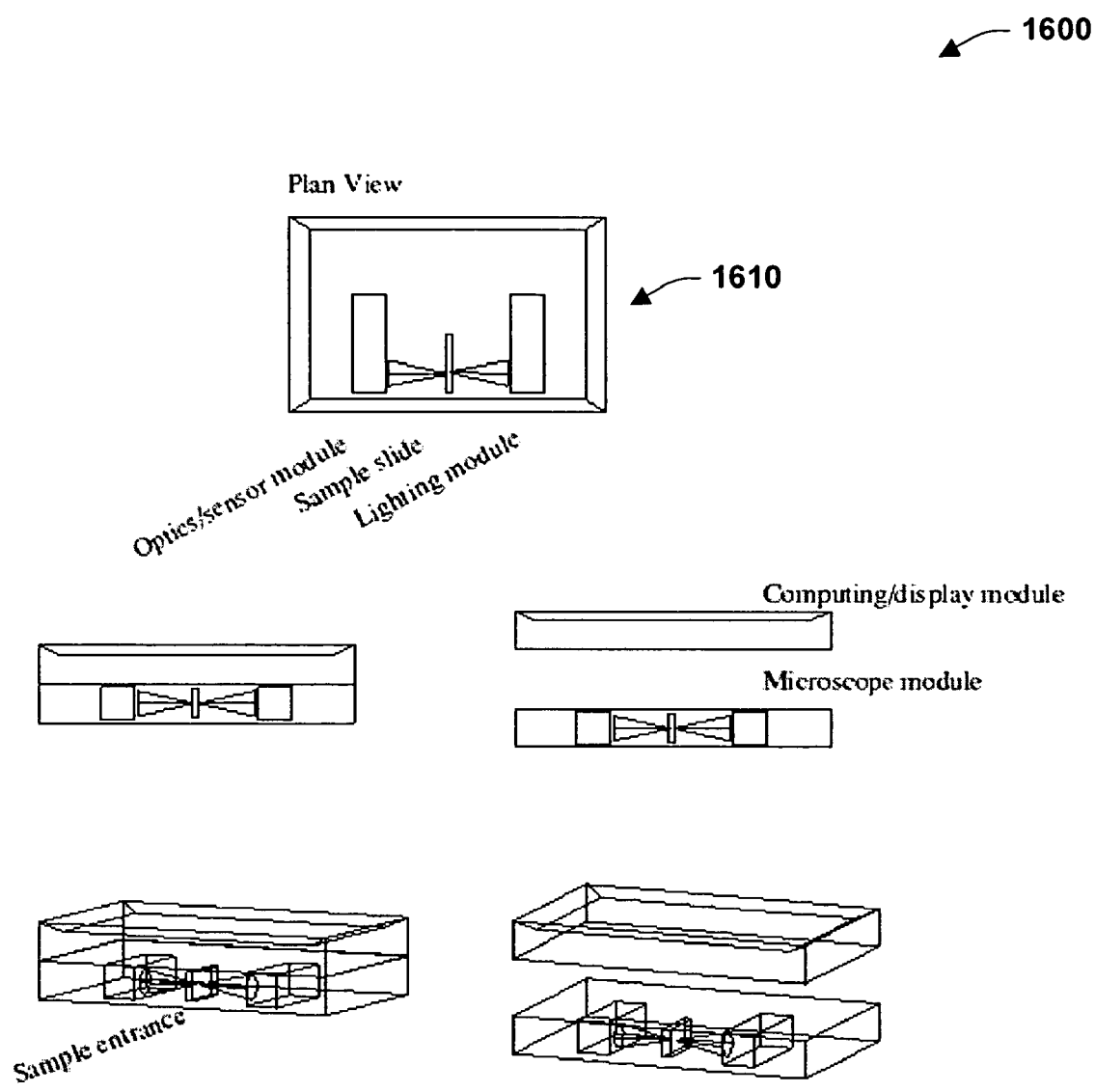

Software:

should be implemented with a simple graphical user interface should be capable of identifying red cells, white cells, and sickle-cells (deformed erythrocytes)

should be capable of performing simple counts and blood differentials should present results visually (displayed image) and textually (data list)

should offer off-line storage on removable media (e.g., floppy disk, memory stick) or as a simple printout should be capable of being expanded via a modular interface to allow for more sophisticated analyses should be capable of being distributed in varying formats (e.g., on a storage medium, as a data stream via remote connection, or as a ROM-module).

should be well-documented and open-source, if possible, to allow for onsite modifications FIG. 16 illustrates a system 1600 that provides the following features:

fully-integrated and portable a baseplate 1610 holding an optics/sensor module, a lighting module, and a sample presentation module single-board computer coupled to baseplate 1610, carrying display (LCD)

expansion unit carrying printer/floppy disk.

What has been described above are preferred aspects of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A portable digital microscope imaging system, comprising:
    a sensor having a plurality of pixels, where the plurality of pixels receive an image of an object that is uniformly illuminated by an input light source; and
    a microscopic optical system that maps the plurality of pixels to an object field of view, where at least one pixel from the plurality of pixels is scaled to about a size of a diffraction-limited spot defined by the microscopic optical system.

2. The system of claim 1, further comprising an excitation source for the microscopic optical system including at least one of a light source, and a Luxeon Star.

3. The system of claim 1, further comprising an enclosure for the microscopic optical system and the sensor.

4. The system of claim 3, further comprising a processor or computer that is adapted for at least one of an operation within the enclosure of the microscopic optical system and an operation external to the enclosure of the microscopic optical system in order to facilitate image generation.

5. The system of claim 2, further comprising a holographic diffuser to facilitate generation of an image.

6. The system of claim 1, the optical system and the sensor are associated with a digital camera.

7. The system of claim 1, the sensor is adapted for at least red, green, blue, and at least one other color.

8. The system of claim 1, the optical system and sensor are employed in at least one of a remote medicine application and an industrial application.

9. The system of claim 1, further comprising at least one of an objective turret, a manual or automatic adjustment, an iris control, a projection module, and an illumination module.

10. The system of claim 1, further comprising at least one of an AC or DC power supply.

11. The system of claim 1, further comprising a port for transferring digital images between locations or devices.

12. The system of claim 11, the port is associated with at least one of a parallel port, a wireless port, a printer port, a USB port, and a Firewire port.

13. A digital microscope camera, comprising:
    a sensor having a plurality of pixels; and
    a microscopic lens configuration that maps the plurality of pixels to an object field of view that is uniformly illuminated, where at least one pixel from the plurality of pixels is correlated to about a size of a diffraction-limited spot defined by the microscopic lens configuration.

14. The digital camera of claim 13, the pixels are associated with at least four colors.

15. A digital microscope imaging system, comprising:
    a light source to uniformly illuminate a specimen;
    a holographic diffuser associated with the light source;
    a microscopic optical medium to magnify the specimen; and
    a sensor having a plurality of pixels for receiving light from the specimen in accordance with the microscopic optical medium, where at least one pixel from the plurality of pixels is correlated to about a size of a diffraction-limited spot defined by the microscopic optical medium.

16. The system of claim 15, further comprising a memory to store information from the pixels.

17. The system of claim 15, the optical system and the sensor are associated with a digital camera.

18. The system of claim 15, further comprising at least one of an AC or DC power supply.

19. The system of claim 15, further comprising a port for transferring digital images between locations or devices.

20. The system of claim 19, the port is associated with at least one of a parallel port, a wireless port, a printer port, a USB port, and a Firewire port.

* * * * *